United States Patent
Zankowski et al.

(10) Patent No.: US 11,011,264 B2
(45) Date of Patent: May 18, 2021

(54) RADIOTHERAPY TREATMENT PLANNING USING ARTIFICIAL INTELLIGENCE (AI) ENGINES

(71) Applicant: Varian Medical Systems International AG, Palo Alto, CA (US)

(72) Inventors: Corey Zankowski, Palo Alto, CA (US); Charles Adelsheim, Mountain View, CA (US); Joakim Pyyry, Helsinki (FI); Esa Kuusela, Espoo (FI)

(73) Assignee: VARIAN MEDICAL SYSTEMS INTERNATIONAL AG

( * ) Notice: Subject to any disclaimer, the term of this patent is extended or adjusted under 35 U.S.C. 154(b) by 347 days.

(21) Appl. No.: 16/102,767

(22) Filed: Aug. 14, 2018

(65) Prior Publication Data

US 2019/0074079 A1 Mar. 7, 2019

Related U.S. Application Data

(60) Provisional application No. 62/542,810, filed on Aug. 9, 2017.

(51) Int. Cl.
| | |
|---|---|
| *A61N 5/10* | (2006.01) |
| *G16H 20/40* | (2018.01) |
| *G06N 20/00* | (2019.01) |
| *G06K 9/62* | (2006.01) |

(Continued)

(52) U.S. Cl.
CPC ........... *G16H 20/40* (2018.01); *A61N 5/1039* (2013.01); *G06K 9/6265* (2013.01); *G06K 9/6288* (2013.01); *G06N 5/02* (2013.01); *G06N 20/00* (2019.01); *G16H 50/20* (2018.01); *G06K 2209/05* (2013.01)

(58) Field of Classification Search
CPC .................. A61N 5/103; A61N 5/1039; A61N 2005/1041; G06T 7/0012; G06F 19/34; G06F 19/3443; G16H 50/70
See application file for complete search history.

(56) References Cited

U.S. PATENT DOCUMENTS

| | | | |
|---|---|---|---|
| 9,123,097 B2 * | 9/2015 | Lee | A61N 5/103 |
| 9,463,334 B2 * | 10/2016 | Kuusela | G06N 5/022 |
| 2005/0147291 A1 | 7/2005 | Huang et al. | |

(Continued)

OTHER PUBLICATIONS

Hui Yan et al., "AI-guided Parameter Optimization in Inverse Treatment Planning", Physics in Medicine & Biology, 2003, pp. 3565-3580, vol. 48.

*Primary Examiner* — Samuel G Gilbert
(74) *Attorney, Agent, or Firm* — Su IP Consulting

(57) ABSTRACT

Example methods and systems for radiotherapy treatment planning are provided. One example method may comprise obtaining image data associated with a patient; and processing the image data to generate a treatment plan for the patient using an inferential chain that includes multiple AI engines that are trained separately to perform respective multiple treatment planning steps. A first treatment planning step may be performed using a first AI engine to generate first output data based on at least one of: (i) the image data, and (ii) first input data generated based on the image data. A second treatment planning step may be performed using a second AI engine to generate the treatment plan based on at least one of: (i) the first output data, and (ii) second input data generated based on the first output data.

21 Claims, 12 Drawing Sheets

(51) Int. Cl.
*G16H 50/20* (2018.01)
*G06N 5/02* (2006.01)

(56) References Cited

U.S. PATENT DOCUMENTS

| | | |
|---|---|---|
| 2014/0371256 A1 | 12/2014 | Sadhasivam et al. |
| 2016/0016008 A1* | 1/2016 | Kelly .................. A61N 5/1083 600/1 |
| 2018/0046942 A1 | 2/2018 | Conroy et al. |
| 2019/0051398 A1 | 2/2019 | Zankowski et al. |

* cited by examiner

200 

```
┌─────────────────────────────────────────┐
│  Obtain image data associated with patient │
│                   210                   │
└─────────────────────────────────────────┘
                    │
                    ▼
┌─────────────────────────────────────────┐
│  Process image data to generate treatment plan │
│       using inferential chain that includes    │
│              multiple AI engines               │
│                   220                          │
│  ┌───────────────────────────────────────┐    │
│  │ Perform, using first AI engine, first │    │
│  │ treatment planning step to generate   │    │
│  │ first output data based on at least   │    │
│  │ one of: (i) image data and (ii) first │    │
│  │ input data generated based on         │    │
│  │ image data                            │    │
│  │                 230                   │    │
│  └───────────────────────────────────────┘    │
│  ┌───────────────────────────────────────┐    │
│  │ Perform, using second AI engine,      │    │
│  │ second treatment planning step to     │    │
│  │ generate treatment plan based on      │    │
│  │ at least one of: (i) first output     │    │
│  │ data and (ii) second input data       │    │
│  │ generated based on first output data  │    │
│  │                 240                   │    │
│  └───────────────────────────────────────┘    │
└─────────────────────────────────────────┘
```

FIG. 2

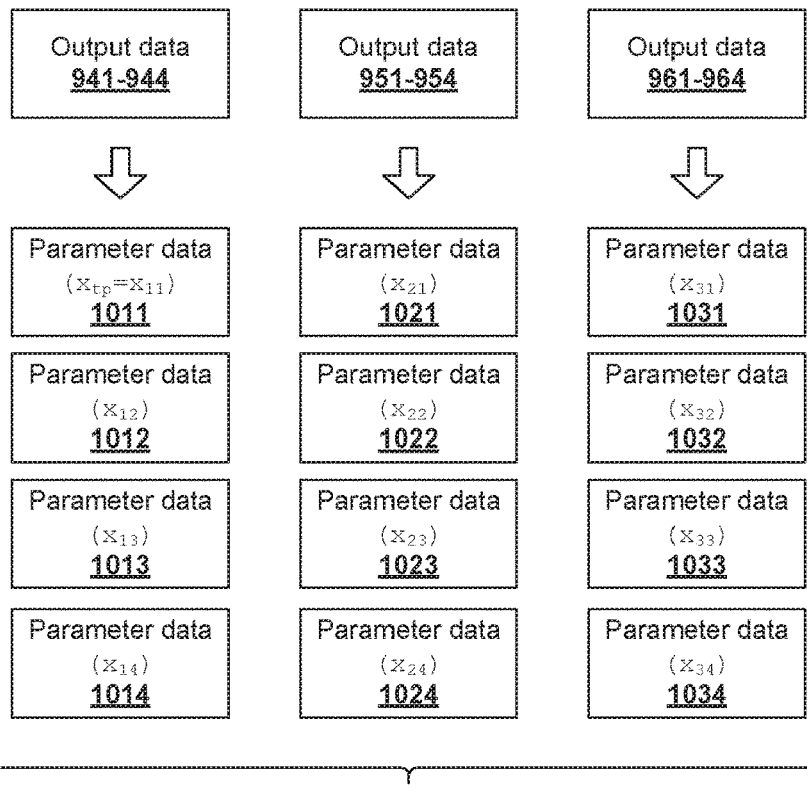
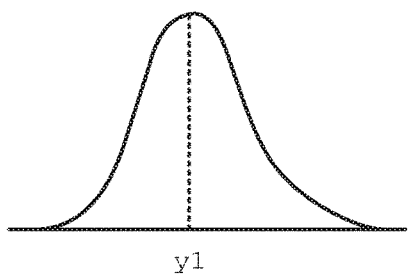 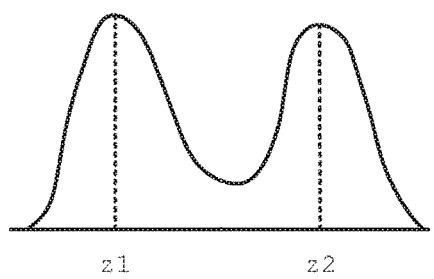
 
FIG. 10

RADIOTHERAPY TREATMENT PLANNING USING ARTIFICIAL INTELLIGENCE (AI) ENGINES

CROSS-REFERENCE TO RELATED APPLICATIONS

The present application claims the benefit of the U.S. Provisional Application No. 62/542,810 filed on Aug. 9, 2017. The provisional application, including any appendices or attachments thereof, is hereby incorporated by reference in their entirety. The present application is related in subject matter to U.S. patent application Ser. No. 16/102,770, which is incorporated herein by reference.

BACKGROUND

Unless otherwise indicated herein, the approaches described in this section are not prior art to the claims in this application and are not admitted to be prior art by inclusion in this section.

Radiotherapy is an important part of a treatment for reducing or eliminating unwanted tumors from patients. Unfortunately, applied radiation does not inherently discriminate between an unwanted tumor and any proximal healthy structures such as organs, etc. This necessitates careful administration to restrict the radiation to the tumor (i.e., target). Ideally, the goal is to deliver a lethal or curative radiation dose to the tumor, while maintaining an acceptable dose level in the proximal healthy structures. However, to achieve this goal, conventional radiotherapy treatment planning may be time and labor intensive.

SUMMARY

According to examples of the present disclosure, radiotherapy treatment planning may be improved using artificial intelligence (AI) techniques. According to a first aspect of the present disclosure, example methods and systems for radiotherapy treatment planning are provided. One example method may comprise obtaining image data associated with a patient; and processing the image data to generate a treatment plan for the patient using an inferential chain that includes multiple AI engines, which are trained separately to perform respective multiple treatment planning steps. A first treatment planning step may be performed using a first AI engine to generate first output data based on at least one of: (i) the image data, and (ii) first input data generated based on the image data. A second treatment planning step may be performed using a second AI engine to generate the treatment plan based on at least one of: (i) the first output data, and (ii) second input data generated based on the first output data. Various examples will be discussed using FIG. 1 to FIG. 6.

According to a second aspect of the present disclosure, example methods and systems for generating an aggregated AI engine for radiotherapy treatment planning are provided. One example method may comprise obtaining multiple AI engines associated with respective multiple treatment planners. The multiple AI engines may be trained to perform a particular treatment planning step, and each of the multiple AI engines is trained to emulate one of the multiple treatment planners performing the particular treatment planning step. The example method may further comprise generating multiple sets of output data using the multiple AI engines associated with the respective multiple treatment planners: comparing the multiple AI engines associated with the respective multiple treatment planners based on the multiple sets of output data; and based on the comparison, aggregating at least some of the multiple AI engines to generate an aggregated AI engine for performing the particular treatment planning step. Various examples will be discussed using FIG. 7 to FIG. 11. As will be discussed below, the term "treatment planner" (or more simply "planner") may refer to an individual (e.g., clinical expert), a group of individuals, multiple groups, a clinical site or institution (e.g., research institution, university), a network of sites, etc.

BRIEF DESCRIPTION OF THE DRAWINGS

FIG. 2 is a flowchart of an example process for a computer system to perform radiotherapy treatment planning using AI engines;

FIG. 10 is a schematic diagram illustrating example AI engine comparison according to the example in FIG. 8;

DETAILED DESCRIPTION

The technical details set forth in the following description enable a person skilled in the art to implement one or more embodiments of the present disclosure.

Figure 1:
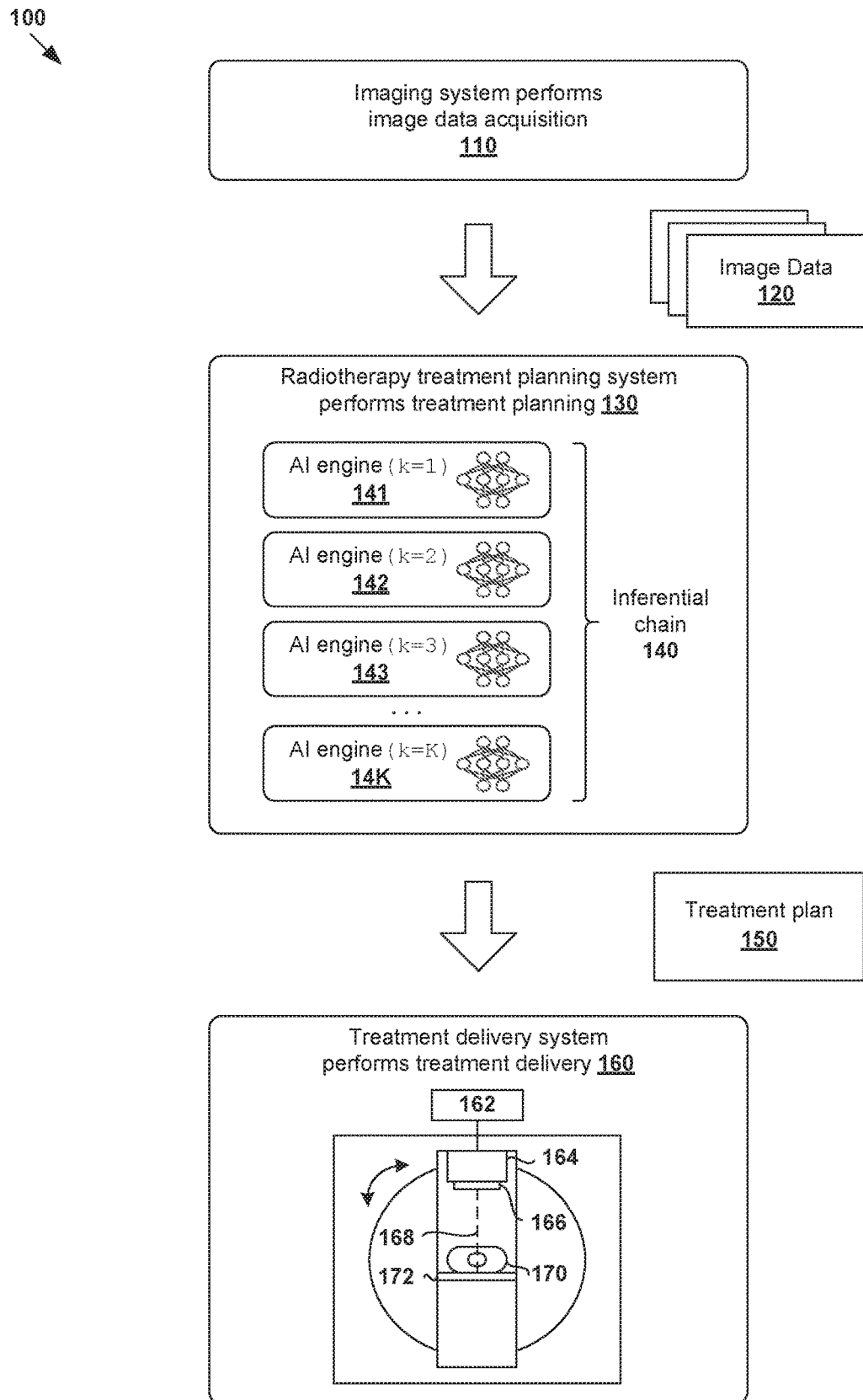
FIG. 1 is a schematic diagram illustrating an example process flow for radiotherapy treatment.

FIG. 1 is a schematic diagram illustrating example process flow 100 for radiotherapy treatment. Example process 100 may include one or more operations, functions, or actions illustrated by one or more blocks. The various blocks may be combined into fewer blocks, divided into additional blocks, and/or eliminated based upon the desired implementation. In the example in FIG. 1, radiotherapy treatment generally includes various stages, such as an imaging system performing image data acquisition for a patient (see 110); a radiotherapy treatment planning system (see 130) generating a suitable treatment plan (see 150) for the patient; and a treatment system (see 160) delivering treatment according to the treatment plan.

In more detail, at 110 in FIG. 1, image data acquisition may be performed using an imaging system to capture image data 120 of a patient (particularly the patient's anatomy) that requires treatment. Any suitable medical image modality or modalities may be used, such as computed tomography (CT), cone beam computed tomography (CBCT), positron emission tomography (PET), magnetic resonance imaging (MRI), single photon emission computed tomography (SPECT), any combination thereof, etc. For example, when CT or MRI is used, image data 120 may include a series of two-dimensional (2D) images or slices, each representing a cross-sectional view of the patient's anatomy, or may include volumetric or three-dimensional (3D) images of the patient, or may include a time series of 2D or 3D images of the patient (e.g., four-dimensional (4D) CT or 4D CBCT).

At 130 in FIG. 1, based on image data 120, radiotherapy treatment planning may be performed to generate treatment plan 150 for the patient. Treatment plan 150 is generated to deliver radiation to a "target" representing, for example, a malignant tumor requiring treatment (e.g., prostate tumor, etc.), while restricting radiation to a proximal healthy structure (e.g., rectum, bladder, etc.). The healthy structure that might be adversely affected by the radiation is known as an organ-at-risk (OAR) delineated organ, non-target structure (e.g., bone, tissue, etc.), etc. The radiation may be designed to be curative, palliative, adjuvant, etc. Depending on the desired implementation, radiotherapy treatment planning at block 130 may be performed based on any additional and/or alternative data, such as prescription, disease staging, biologic or radiomic information, genetic information, assay information, biopsy information, past treatment or medical history, any combination thereof, etc.

Treatment plan 150 may include 2D fluence map data for a set of beam orientations or angles. Each fluence map specifies the intensity and shape (e.g., as determined by a multileaf collimator (MLC)) of a radiation beam emitted from a radiation source at a particular beam orientation and at a particular time. For example, in practice, intensity modulated radiotherapy treatment (IMRT) or any other treatment technique(s) may involve varying the shape and intensity of the radiation beam while at a constant gantry and couch angle. Alternatively or additionally, treatment plan 150 may include machine control point data (e.g., jaw and leaf positions), volumetric modulated arc therapy (VMAT) trajectory data for controlling a treatment system, etc. In practice, block 130 may be performed based on goal doses prescribed by a clinician (e.g., oncologist, dosimetrist, planner, etc.), such as based on the clinician's experience, the type and extent of the tumor, patient geometry and condition, etc.

At 160 in FIG. 1, treatment delivery is performed to deliver radiation to the patient according to treatment plan 150. For example, radiotherapy treatment system 160 may include rotatable gantry 164 to which radiation source 166 is attached. During treatment delivery, gantry 164 is rotated around patient 170 supported on structure 172 (e.g., table) to emit radiation beam 168 at various beam orientations according to treatment plan 150. Controller 162 may be used to retrieve treatment plan 150 and control gantry 164, radiation source 166 and radiation beam 168 to deliver radiotherapy treatment according to treatment plan 150.

It should be understood that any suitable radiotherapy treatment system(s) may be used, such as mechanic-arm-based systems, tomotherapy type systems, brachy, sirex spheres, any combination thereof, etc. Additionally, examples of the present disclosure may be applicable to particle delivery systems (e.g., proton, carbon ion, etc.). Such systems may employ either a scattered particle beam that is then shaped by a device akin to an MLC, or may instead employ a scanning beam of adjustable energy, spot size, and dwell time.

Conventionally, radiotherapy treatment planning at block 130 in FIG. 1 is generally time and labor intensive. For example, it usually requires a team of highly skilled and trained oncologists and dosimetrists to manually delineate structures of interest by drawing contours or segmentations on image data 120. These structures are manually reviewed by a physician, possibly requiring adjustment or re-drawing. After the structures are agreed upon, there are additional labor-intensive steps to process the structures to generate a clinically-optimal treatment plan specifying beam orientations and trajectories, as well as corresponding 2D fluence maps. These steps are often complicated by a lack of consensus among different physicians and/or clinical sites as to what constitutes "good" contours or segmentation. While it is possible to reduce the amount of manual work by formulating the treatment planning process as an optimization problem, it is not always clear which solution is "optimal" and how to instruct an optimizer to find that solution. Additionally, the optimization space may include one or more local minimums which are not the global minimum, but which none-the-less an optimizer may converge on.

Another challenge is the inconsistency of radiotherapy treatment planning. In practice, there might be a huge variation in the way structures or segments are drawn by different clinical experts, which results in uncertainty in target volume size and shape, as well as the exact proximity, size and shape of OARs that should receive minimal radiation dose. Even for a particular clinical expert, there might be variation in the way segments are drawn on different days. Also, there may be variation in the "optimal" 3D dose distributions designed by clinical experts based on a set of identical structure volumes, which is exacerbated when there are large variations in the way the structures are drawn. For example, a plan created for a patient at Institution A may differ considerably from another plan created for the same patient at Institution B. These factors result in wild variations in the plan quality generated for a single patient, when considered over time, across experts, and between sites. This might in turn result in sub-optimal clinical outcomes for the patient, which is undesirable.

A further challenge is that there is no "gold standard" for treatment planning. For example, it is generally impossible to define a standard for target delineation because tumors present differently in every patient. Also, there is no single gold standard for the delineation of healthy tissues, no single technique to treat a given disease site with radiation, and no gold standard approach for optimizing treatment parameters, even when the same technique is applied. The challenges discussed above make radiotherapy treatment planning a very complex process.

According to examples of the present disclosure, artificial intelligence (AI) techniques may be applied to ameliorate various challenges associated with radiotherapy treatment planning. In particular, AI techniques may be used to automate the process of transforming image data 120 to treatment plan 150 that is clinically acceptable and optimal for a given patient. This improves the efficiency of radiotherapy treatment planning and possibly the treatment outcome, such as increasing the tumor control probability and/or reducing the likelihood of health complications or death due to radiation overdose in the healthy structures.

Figure 11:
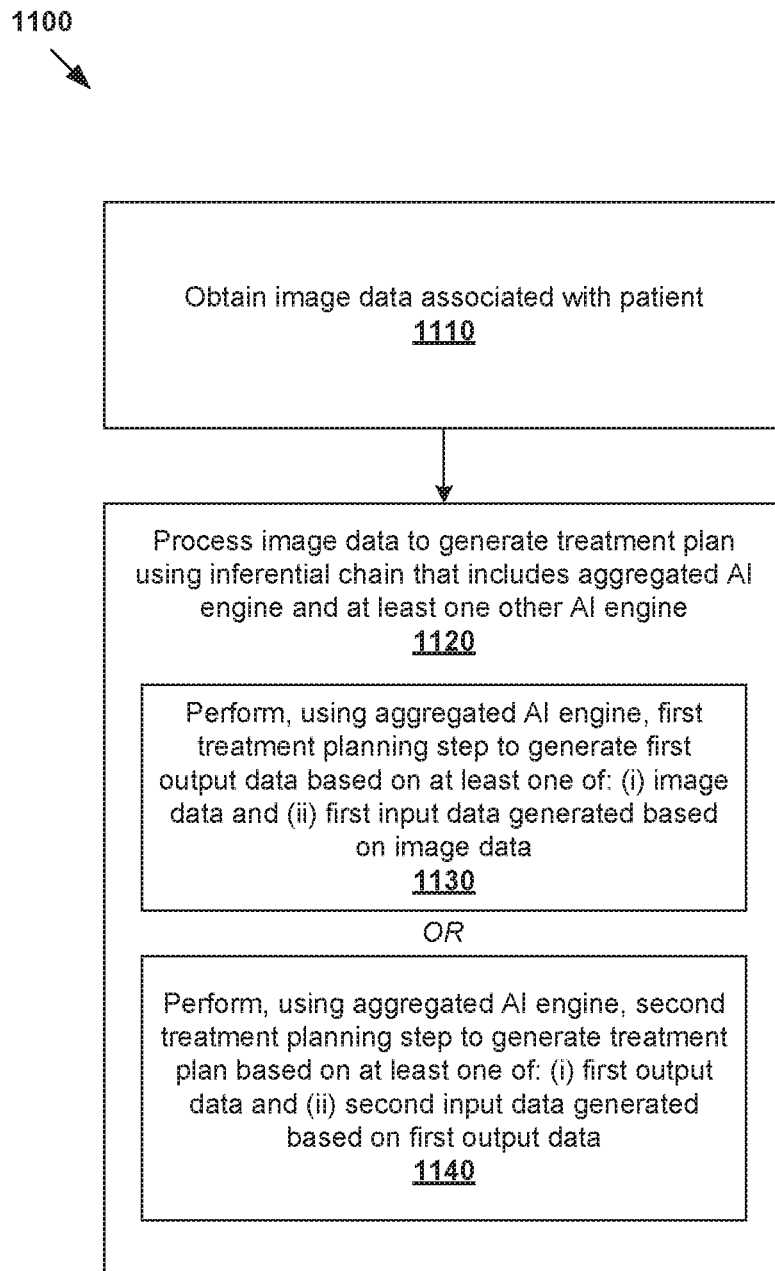
FIG. 11 is a flowchart of an example process for a computer system to perform radiotherapy treatment planning using an aggregated AI engine.
Figure 12:
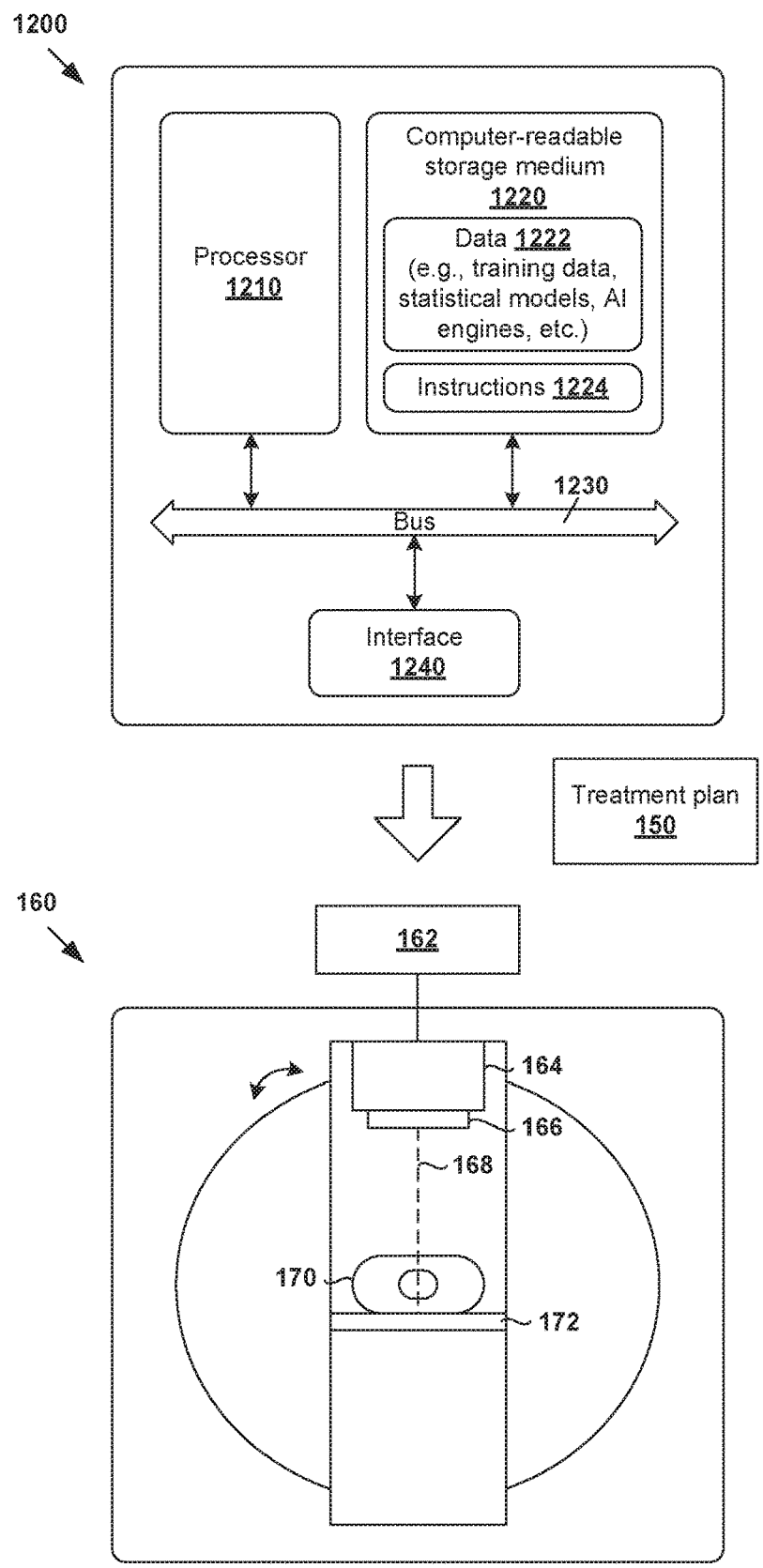
FIG. 12 is a schematic diagram of an example computer system to perform radiotherapy treatment planning.

In the following, various examples will be discussed below using FIG. 1 to FIG. 12. In particular, radiotherapy treatment planning using multiple AI engines will be discussed using FIG. 1 to FIG. 6. Further, AI engine aggregation for radiotherapy treatment planning will be discussed using FIG. 7 to FIG. 11. Examples of the present disclosure may be implemented using any suitable computer system(s), an example of which is shown in FIG. 12.

Radiotherapy Treatment Planning using Inferential Chain

According to a first aspect of the present disclosure, radiotherapy treatment planning may be improved by dividing a planning process into distinct, trainable treatment planning steps that are implemented using multiple AI engines. For example in FIG. 1, radiotherapy treatment planning may be performed using inferential chain 140 that includes multiple AI engines (see 141-14K), where K≥2 represents the number of steps and corresponding AI engines trained to perform the steps.

An example with K=2 is shown in FIG. 2, which is a flowchart of example process 200 for a computer system to perform radiotherapy treatment planning using AI engines. Example process 200 may include one or more operations, functions, or actions illustrated by one or more blocks, such as 210 to 240. The various blocks may be combined into fewer blocks, divided into additional blocks, and/or eliminated based upon the desired implementation. Examples of the present disclosure may be implemented using any suitable computer system, an example of which will be discussed using FIG. 12.

At 210 in FIG. 2, image data 120 associated with a patient may be obtained. At 220 in FIG. 2, image data 120 may be processed using an inferential chain (see 140 in FIG. 1) to generate treatment plan 150 for the patient. Inferential chain 140 includes multiple AI engines 141-14K that are trained separately. Each $k^{th}$ AI engine may be trained to perform a $k^{th}$ treatment planning step of the planning process (k=1, 2, . . . , K). For example, at 230 in FIG. 2, a first AI engine may perform a first treatment planning step to generate first output data based on at least one of: (i) image data 120 and (ii) first input data generated based on image data 120. Further, at 240 in FIG. 2, a second AI engine may perform a second treatment planning step to generate treatment plan 150 based on at least one of: (i) the first output data of the first AI engine and (ii) second input data generated based on the first output data.

As will be discussed using further using FIG. 4, the "first AI engine" may be trained to perform segmentation based on image data 120. In another example, the "first AI engine" may be trained to perform 3D dose prediction based on input data=structure data, which may be generated based on image data 120. In a further example, the "first AI engine" may be trained to perform structure projection estimation based on input data=3D dose data, which may be generated based on the structure data and image data 120. The "second AI engine" may be trained to generate treatment plan 150 based on the output data (e.g., 3D dose data, structure projection data, etc.) generated by the first AI engine. Alternatively and/or additionally, the second AI engine may be trained using any data generated based on the output data of the first AI engine.

Examples of the present disclosure should be contrasted against conventional approaches (e.g., brute force approaches) that train a single AI engine to learn all correlations and associations between image data 120 and the final treatment plan 150, which may comprise 2D fluence maps and machine trajectories. Although theoretically possible, these conventional approaches are highly complex, and require increased amount of computer memory and processing power. Also, it is unlikely for these conventional approaches to yield results because a large number of training datasets (e.g. patient cases) are required to train the AI engine of that complexity, possibly exceeding the total number of curated treatment plans stored in databases around the world.

Instead of training a single neural network that transforms image data 120 to treatment plan 150 directly, AI engines 141-14K may be trained separately and independently from each other, each using a reduced and more manageable number of training datasets. This approach of "discretizing" the planning process using inferential chain 140 reduces the complexity of computer-implemented radiotherapy treatment planning. It should be understood that any suitable K may be selected, and it is not necessary to perform each and every step of a radiotherapy treatment planning process using an AI engine. For example, if the process involves L steps, K<L steps may be implemented using K AI engines. The remaining steps (i.e., L-K) may be performed using any other approach, such as by hand, or by using optimization system(s), knowledge-based system(s), etc.

As used herein, the term "inferential chain" may refer generally to a set of AI engines that are each trained to perform a step, an intermediate step or a sub-step associated with radiotherapy treatment planning. The term "AI engine" may refer to any suitable hardware and/or software component(s) of a computer system that are capable of executing algorithms according to an AI model. Any suitable AI model(s) may be used, such as neural network, deep learning system, Bayes classifier, decision tree, discriminant analysis, fuzzy logic, etc. Different AI engines may apply the same AI model, or different models. Each AI engine may employ any suitable learning model, such as supervised learning, unsupervised learning, semi-supervised learning, reinforcement learning, etc.

For example, an AI engine may be a neural network, which refers generally to a network of processing elements (called "neurons," "nodes," etc.) that are interconnected via connections (called "synapses," "weights," etc.). Any suitable neural network technique(s) may be used, such as feed forward, radial basis network, deep feed forward, recurrent neural network, long or short term memory, gated recurrent unit, auto encoder (AE), variational AE, denoising AE, sparse AE, Markov chain, Hopfield network, Boltzmann machine, restricted machine, deep belief network, deep convolutional network, deconvolutional network, deep convolutional inverse graphics network, generative adversarial network, liquid state machine, extreme learning machine, echo state network, deep residual network, Kohonen network, support vector machine (SVM), neural Turing machine, or a combination thereof, etc. For example, convolutional neural networks based on any suitable architecture(s) may be used, such as LeNet, AlexNet, ResNet, U-net, V-net, DenseNet, etc.

Various examples of the "AI engines," "first treatment planning step," "first input data," "first output data," "second treatment planning step," and "second input data" mentioned in FIG. 2 will be discussed below. Examples relating to segmentation, 3D dose prediction, structure projection data estimation and treatment plan generation will be discussed using FIG. 4 and FIG. 5. Examples relating to clinical goal estimation, patient outcome prediction, proton dose estimation, and proton layer spot data estimation will be discussed using FIG. 6.

Training and Validation

During a training phase, AI engines 141-14K may be trained using training data and/or statistical model(s), and validated using statistical model(s) and/or validation data.

Figure 3:
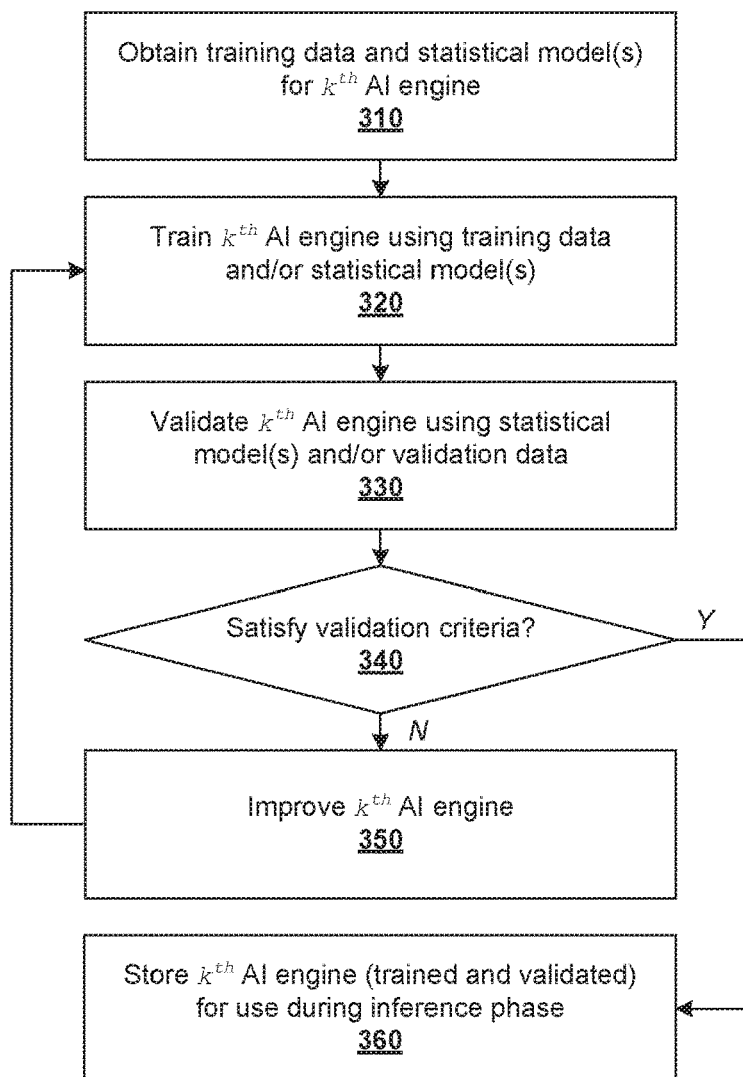
FIG. 3 is a flowchart of an example process for training and validating multiple AI engines for radiotherapy treatment planning.

FIG. 3 is a flowchart of example process 300 for training and validating multiple AI engines for radiotherapy treatment planning. Example process 300 may include one or more operations, functions, or actions illustrated by one or more blocks, such as 310 to 360. The various blocks may be combined into fewer blocks, divided into additional blocks, and/or eliminated based upon the desired implementation. Blocks 310-360 may be performed for each and every $k^{th}$ AI engine in inferential chain 140. This way, AI engines 141-14K may be trained and validated separately, such as using the same computer system or different computer systems.

At 310 and 320 in FIG. 3, training data and/or statistical model(s) may be obtained to train a particular $k^{th}$ AI engine, where k=1, 2, . . . , K. The training data may be user-generated through observations and experience, or machine-generated. The training data may be extracted from past treatment plans developed for past patients. For example, using supervised learning, the training data may include labeled data specifying known input-output ($I_k$, $O_k$) mappings, where $I_k$=input data to the $k^{th}$ AI engine and $O_k$=output data from the $k^{th}$ AI engine. Note that $I_k$ and $O_k$ may be a single value (i.e., scalar) or a vector of multiple values. During the training phase, the $k^{th}$ AI engine is trained to learn a function $f(I_k) \approx O_k$ that maps or transforms the input data ($I_k$) to the output data ($O_k$). Additionally or alternatively, using reinforcement learning, statistical model(s) may be used to guide the training process at block 320, such as to favor solutions having certain statistical properties.

At 330 in FIG. 3, validation may be performed to validate the $k^{th}$ AI engine using statistical model(s) and/or validation data. Validation may be performed to improve results, such as to prevent overfitting or falling into a local minimum, provide an indication of convergence, etc. Validation data may include labeled data (e.g., known input-output mappings) that was not used during training at block 320. This way, output data generated by the $k^{th}$ AI engine may be compared against known output data.

The term "statistical model" may refer generally to a model for evaluating a probability of certain measurable quantity (also referred to as attribute, feature or parameter) derivable from an intermediate output or final output of the $k^{th}$ AI engine. Depending on the treatment planning step performed by the $k^{th}$ AI engine, a "quantity" evaluated by a statistical model may be one of the following: a dose level of a structure identified from image data 120 (e.g., mean, maximum or minimum dose level); a feature of the structure (e.g., size, shape, texture, principal component analysis, geometric distribution, material density, etc.); distance or relative position between two structures; smoothness of 2D fluence maps; total motion of leaves in VMAT plan, any combination thereof, etc. For clarity, the prior sentence is illustrative only, the statistical model(s) may be any analogous model as known in the art.

The "probability" evaluated using a statistical model may be unconditional (e.g., describes the statistics of the quantity over the whole set of training data) or conditional (e.g., describes the statistics of some quantity in condition that certain previous intermediate result has been obtained). For example, structure size could be used unconditionally (e.g., it has the same criteria regardless of the CT scan), or it could be conditional to some values derived from the CT scan (e.g., total area of non-zero region in the slice going through the center of the given organ).

Any suitable "statistical model" may be used, ranging from simple metric(s) to more complex model(s). The statistical model may return a single value (i.e., scalar) or multiple values (vector). The returned value(s) may be based on automatic feature extraction process, user-given metrics, etc. For example, an independently-developed set of statistical models may be used to validate results of the $k^{th}$ AI engine. In practice, the term "independently-developed" may refer to inference-related independence (e.g., statistical models that are developed based on different sets of data or assumptions), approach-related independence, etc. In general, independence may indicate that the training sets are different, but may also indicate that different approaches are used to create the statistical models. This way, the statistical model(s) may be used to evaluate the reliability or validity of an AI engine. Any dependence among the statistical models may reduce the amount of additional information that may be gained using several models in the inference. Using statistical models, an AI engine may be trained more quickly, either fully or partially based on unsupervised data. The statistical models may include "simple" models that require fewer datasets to develop. Also, the statistical models may be deployed clinically to simplify or automate parts of the radiotherapy treatment planning process before AI training achieves clinical acceptability.

Depending on the desired implementation, a particular $k^{th}$ AI engine may be initially validated using a variety of basic, sparse statistical models. The statistical models may also be used to bootstrap the training process at block 320, as well as for evaluating the performance of the AI engines at 330. For example, the statistical models may serve as a feedback mechanism to accelerate training, such as by backpropagation, etc. Using a variety of statistical models, each AI engine may be trained more rapidly using a relatively small number of datasets. The independently-developed set of statistics that may eventually replace human reviewers, or minimize their involvement, to monitor a continuous learning process that is suitable or ideal for creating a powerful AI system.

At 340 and 350 in FIG. 3, in response to determination that the $k^{th}$ AI engine does not satisfy certain validation criteria, the training phase continues by improving $k^{th}$ AI engine for the next iteration. Any suitable improvement(s) may be made at block 350. For example, the training data may be updated to increase or reduce the amount of labeled data, to include alternative labeled data, etc. In another example, outlier cases in the training data may be identified, and removed if necessary. Further, the network architecture or model (hyper) parameters of the $k^{th}$ AI engine may be updated.

Blocks 320-350 may be repeated until the $k^{th}$ AI engine is fully trained and satisfies the validation criteria at block 340. In this case, at 360 in FIG. 3, the trained and validated $k^{th}$ AI engine is stored for use during an inference phase, which may refer generally to a phase where the $k^{th}$ AI engine is used to infer or generate new output data based on its training. Alternatively, the training and validation process may be stopped when certain stopping criteria are met, such as when the $k^{th}$ AI engine stops improving or starts to show signs of overfitting. An AI engine that fails the validation process will not be released for use.

Example AI Engines

Figure 4:
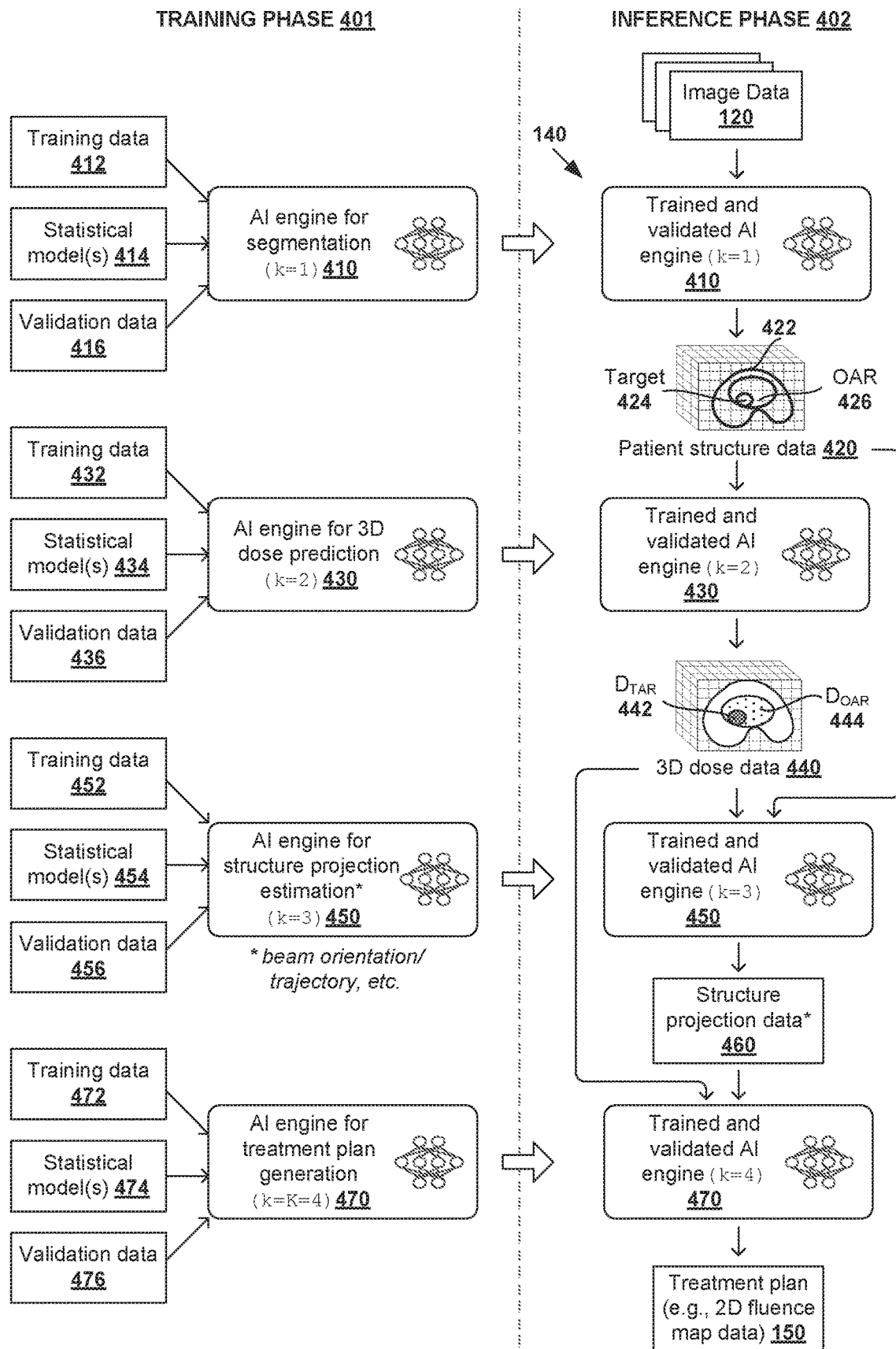
FIG. 4 is a schematic diagram illustrating a first example inferential chain that includes multiple AI engines for radiotherapy treatment planning.

FIG. 4 is a schematic diagram illustrating first example inferential chain 140 that includes multiple AI engines for radiotherapy treatment planning. In this example, radiotherapy treatment planning is divided into K=4 steps: segmentation (k=1), 3D dose prediction (k=2), structure projection data estimation (k=3), and treatment plan generation (k=4). In this case, four AI engines (see 410, 430, 450, 470) are trained separately during training phase 401. Once trained and validated, the AI engines may be used to perform respective treatment planning steps during inference phase 402.

In particular, the AI engines may be interconnected during inference phase 402 to generate treatment plan 150 based on, at least in part, image data 120. For example, first AI engine 410 may be connected with both second AI engine 430 and third AI engine 450; second AI engine 430 with third AI engine 450 and four AI engine 470; and third AI engine 450 with fourth AI engine 470. Any additional and/or alternative input data may be used by AI engine 410/430/450/470. For example, as discussed using FIG. 1, treatment plan 150 may be generated using additional input data such as prescription, dose limits, etc. In practice, each AI engine 410/430/450/470 may include multiple sub-AI-engines. For example, in the case of segmentation (k=1), first AI engine 410 may include multiple sub-AI-engines to segment respective structures (e.g., one to segment prostate, one to segment rectum, etc.).

(a) Segmentation (k=1)

First AI engine 410 is trained to perform segmentation to generate output data $O_k$=patient structure data 420 (i.e., "first output data" in FIG. 2; also referred to as "structure data") based on input data $I_k$=image data 120. Here, image data 120 may be 2D or 3D images of a patient's anatomy. In practice, a 3D volume of the patient that will be subjected to radiation is known as a treatment volume, which may be divided into multiple smaller volume-pixels (voxels). Patient structure data 420 may include segmented and labeled images specifying the contour, shape, size and/or location of structure(s) or segment(s) that are identifiable from image data 120, such as patient's anatomy 422, target 424 (also known as a "target volume"), OAR 426, etc. For example, in relation to prostate cancer, target 424 represents a patient's prostate, and OAR 426 a proximal healthy structure such as rectum, bladder, etc. In relation to lung cancer treatment, target 424 may represent cancerous lung tissue, and OAR 426 proximal healthy lung tissue, esophagus, heart, etc. In practice, AI engine 410 may identify multiple targets and OARs of any shapes and sizes from image data 120.

Using the example in FIG. 3, first AI engine 410 may be trained using first training data 412 and/or first statistical model(s) 414, and validated using first statistical model(s) 414 and/or first validation data 416. Training data 412 may include example input-output data pairs, such as CT images, and corresponding segmented and labeled images. Training data 412 may be generated using manual segmentations by medical professionals and/or automatic segmentation by a computer-implemented tool (e.g., Atlas-based), specialized automated algorithms, etc. Automatic segmentation may include both the delineation of critical OARs 426 and targets 424. Validation data 416 used at block 330 may include known input-output mappings that are not used to train first AI engine 410 at block 320.

Statistical model(s) 414 may be used during training and/or validation to evaluate a probability of certain quantity or attribute associated with a patient's structure, such as its shape, size, texture, contour, principal component analysis, material density, geometric distribution, or Hounsfield Units (HU) distribution; relative position of the structure to another structure, etc. For example, in relation to prostate cancer treatment, a simple model may be used to evaluate the sphericity of a prostate (i.e., target 424) identified from image data 120. At the beginning of a training run, one of the validation criteria at block 340 in FIG. 3 may be set to a probability of 80% spherical. This way, if first AI engine 410 identifies a candidate prostate that is only 10% spherical, it will fail the validation process. The outlier may also be flagged for human review.

(b) 3D Dose Prediction (k=2)

Second AI engine 430 is trained to perform 3D dose prediction to generate output data $O_k$=3D dose data 440 ("first output data" in FIG. 2) based on input data $I_k$=patient structure data 420 ("first input data" in FIG. 2), which is generated based on image data 120. In the example in FIG. 4, 3D dose data 440 may specify 3D dose distributions for respective target 424 (denoted "$D_{TAR}$" at 442) and OAR 426 (denoted "$D_{OAR}$" at 444). Depending on the desired implementation, 3D dose data 440 may include spatial biological effect data (e.g., fractionation corrected dose) and/or cover only part of the treatment volume. For example, the 3D dose prediction may be limited to the vicinity of target(s) 424 or to certain dose levels only. Using AI engine 430, 3D dose distributions may be generated based on segmented patient anatomy in patient structure data 420. Compared to conventional approaches, any intervening optimization step to convert dose volume histograms (DVH) into a 3D dose distribution may be skipped, thereby accelerating the treatment planning process.

According to the example in FIG. 3, second AI engine 430 may be trained using second training data 432 and/or second statistical model(s) 434, and validated using second statistical model(s) 434 and/or second validation data 436. Training data 432 may include actual clinical patient data, and/or automatically-generated data derived from knowledge guided treatment planning using automated scripts. Statistical model(s) 434 may be used to evaluate certain attribute(s) associated with 3D dose data, such as DVH, D20, D50, dose fall-off gradient, etc. For example, the results of second AI engine 430 may be evaluated using a statistical analysis of historical DVH (compression of 3D data into 2D data) to ensure that the predicted 3D dose data matches with the historical experience. The statistical analysis may be performed using any suitable tool, such as knowledge-based planning systems (e.g., RapidPlan™ available from Varian Medical Systems, Inc.). Validation data 436 may include known mapping between patient structure data and corresponding 3D dose data that is not used during training.

(c) Structure Projection Data Estimation (k=3)

Third AI engine 450 is trained to perform structure projection data estimation to generate output data $O_k$=structure projection data 460 ("first output data" in FIG. 2) based on input data $I_k$=patient structure data 420 and 3D dose data 440 ("first input data" in FIG. 2) generated based on image data 120. For example, third AI engine 450 may be trained to select beam orientations and machine trajectories for a treatment system (see 160 in FIG. 1) based on structure(s) identified by first AI engine 410 and 3D dose data 440 determined by second AI engine 430.

Using the example in FIG. 3, third AI engine 450 may be trained using third training data 452 and/or third statistical model(s) 454, and validated using third statistical model(s) 454 and/or third validation data 456. Training data 452 may include actual clinical patient treatment plan data, and/or automatically-generated data, such as using beam orientation or machine trajectory algorithms that meet criteria for clinical acceptability. Any suitable machine trajectory definition algorithms may be used, such as the Trajectory Optimization in Radiotherapy using Sectioning (TORUS) described in U.S. patent application Ser. No. 15/621,962, which is incorporated herein by reference.

Any suitable automated beam orientation selection algorithm may be used to generate training data 432. One example is beam angle optimization (BAO) using Eclipse™ treatment planning system (available from Varian Medical Systems, Inc.). Another example is 4Pi algorithm, which is described in U.S. Provisional Application No. 62/128,906 and PCT Patent Application No. PCT/US2016/020,234 that are incorporated herein by reference. Further, statistical model(s) 454 may be used to evaluate certain attribute(s) associated with the selected beam orientations and/or machine trajectories. Other validation data 456 may include known input-output mappings (i.e., between patient structure data and 3D dose data, and corresponding structure projection data) that are not used during training.

(d) Treatment Plan Generation (k=4)

Fourth AI engine 470 is trained to perform treatment plan generation to generate output data $O_k$=treatment plan 150 based on input data $I_k$=3D dose data 440 and structure projection data 460 ("first output data" or "second input data" in FIG. 2). To achieve a particular 3D dose distribution within the patient, treatment plan 150 may include 2D fluence maps for a set of beam orientations/trajectories, machine control point data (e.g., jaw and leaf positions, gantry and couch positions), etc.

Using the example in FIG. 3, fourth AI engine 470 may be trained using fourth training data 472 and/or fourth statistical model(s) 474, and validated using fourth statistical model(s) 474 and/or fourth validation data 476. Training data 472 may include 2D fluence patterns produced by actual clinical patient treatment plan data. The training process may require multi-parametric analysis of 3D dose data and the projection of target 424 and OAR 426 for each beam oriented around the patient. The approach may be purely model-based, in which case the prediction model is trained to create similar results to an optimization algorithm (e.g., Conjugate Gradient Descent 3D dose optimization algorithm). Alternatively, a combination of model-based and an optimization process may be used. In this case, fourth AI engine 470 may first deduce a general solution for a full non-convex optimization problem, and then an optimization algorithm is used to create the final 2D fluence maps.

Statistical model(s) 474 may be used to evaluate certain attribute(s) associated with the 2D fluence maps in treatment plan 150. Other validation data 476 may include known input-output mappings that are not used during training. For example, results of fourth AI engine 470 may be validated using 2D fluence maps generated entirely using an optimization algorithm. Conjugate Gradient Descent 3D dose optimization algorithm includes a fluence smoothing or normalization term that is known to preserve some of the normal tissue projections in the fluence space. The validation process may involve comparing 3D dose distributions resulting from the 2D fluence maps generated by fourth AI engine 470 against original 3D dose distributions from training data 472 or validation data 476. Instead of, or in addition to, generating 2D fluence maps, fourth AI engine 470 may be trained to generate treatment plan 150 that includes machine control point data (e.g., jaw and leaf positions). It is also possible to deduce some beam geometry parameters at this stage.

Since the relationship between fluence and 3D dose may be mathematically computed by weighting a pencil beam dose kernel by a fluence beamlet, fluence patterns resulting from the optimization process strongly reflect the patient anatomy. According to the example in FIG. 4, the projection of patient anatomy and resulting 3D isodose shapes may be used to train fourth AI engine 470 to automatically generate a 2D fluence map for each beam orientation without the need to iteratively optimize the fluence in the DVH space. By coupling fourth AI engine 470 (i.e., generates 2D fluence maps 150) with second AI engine 430 (i.e., generates 3D dose data 440) during inference phase 402, beam fluences may be generated automatically from patient structure data 420 produced by first AI engine 410 based on image data 120.

(e) Example Treatment Plan

Figure 5:
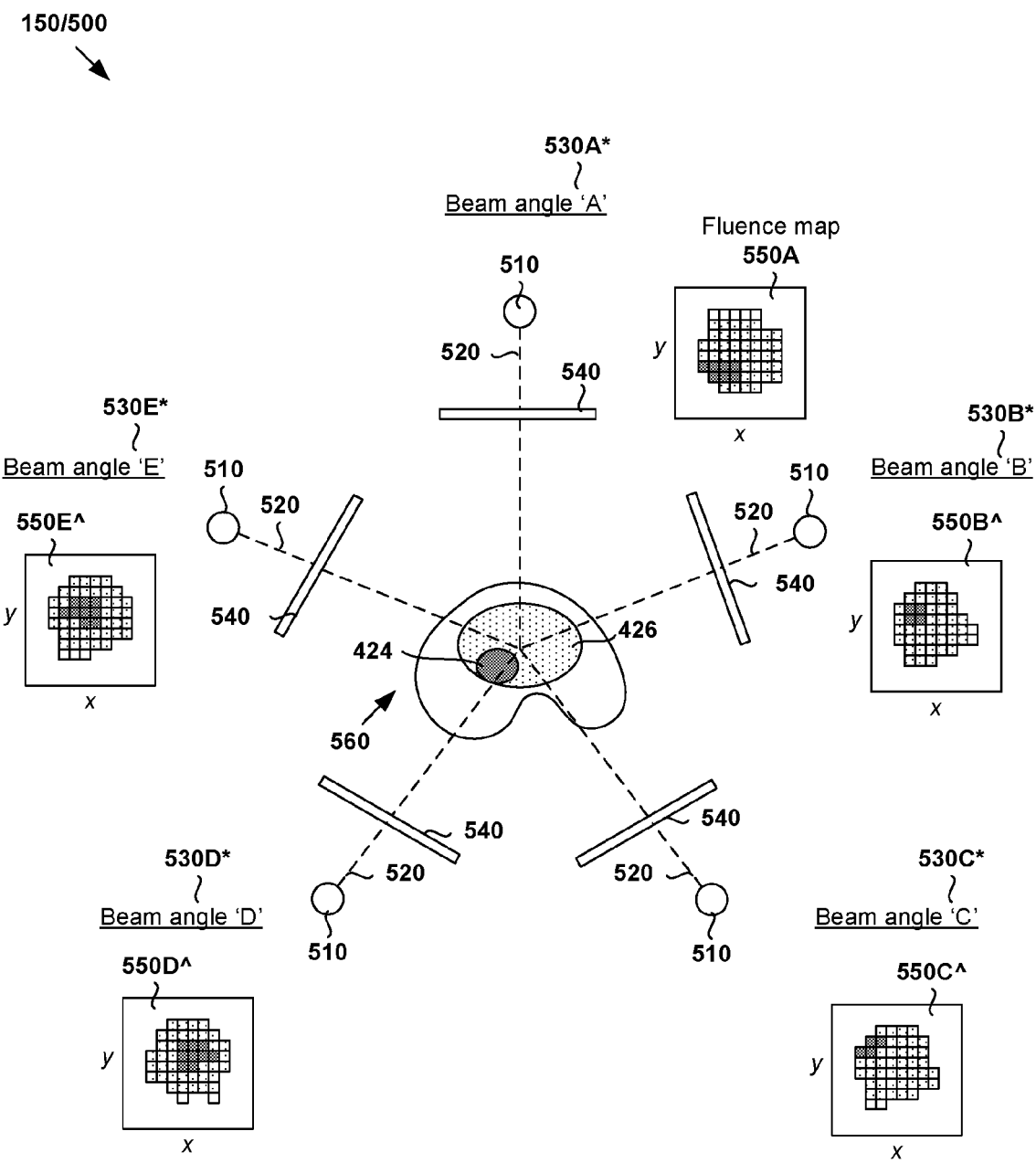
FIG. 5 is a schematic diagram of an example treatment plan generated using an inferential chain with multiple AI engines according to the example in FIG. 4.

FIG. 5 is a schematic diagram of example treatment plan 150/500 generated using an inferential chain with multiple AI engines according to the example in FIG. 4. Treatment plan 150 may be delivered using any suitable treatment system that includes radiation source 510 to project radiation beam 520 onto treatment volume 560 representing the patient's anatomy at various beam angles 530. Although not shown in FIG. 5 for simplicity, radiation source 510 may include a linear accelerator to accelerate radiation beam 520 and a collimator (e.g., MLC) to modify or modulate radiation beam 520. In another example, radiation beam 520 may be modulated by scanning it across a target patient in a specific pattern with various energies and dwell times (e.g., as in proton therapy). A controller (e.g., computer system) may be used to control the operation of radiation source 520 according to treatment plan 150.

During treatment delivery, radiation source 510 may be rotatable using a gantry around a patient, or the patient may be rotated (as in some proton radiotherapy solutions) to emit radiation beam 520 at various beam orientations or angles relative to the patient. For example, five equally-spaced beam angles 530A-E (also labelled "A," "B," "C," "D" and "E") may be selected using third AI engine 430 in FIG. 4. In practice, any suitable number of beam and/or table or chair angles 530 (e.g., five, seven, etc.) may be selected. At each beam angle, radiation beam 520 is associated with fluence plane 540 (also known as an intersection plane) situated outside the patient envelope along a beam axis extending from radiation source 510 to treatment volume 560. As shown in FIG. 5, fluence plane 540 is generally at a known distance from the isocenter.

Using the example in FIG. 4, second AI engine 430 may be trained to estimate 3D dose data based on beam angles 530A-E. The output of fourth AI engine 470 may include 2D fluence maps 550A-E for corresponding beam angles 530A-E. Each fluence map (e.g., 550A) may specify fluence parameters required for treatment delivery, such as the intensity profile of radiation beam 520 at each point on fluence plane 540 at a particular beam angle (e.g., 530A). The radiation dose deposited onto the patient according to fluence maps 550A-E should, as much as possible, correspond to desired 3D dose distributions.

(f) Variations

Figure 6:
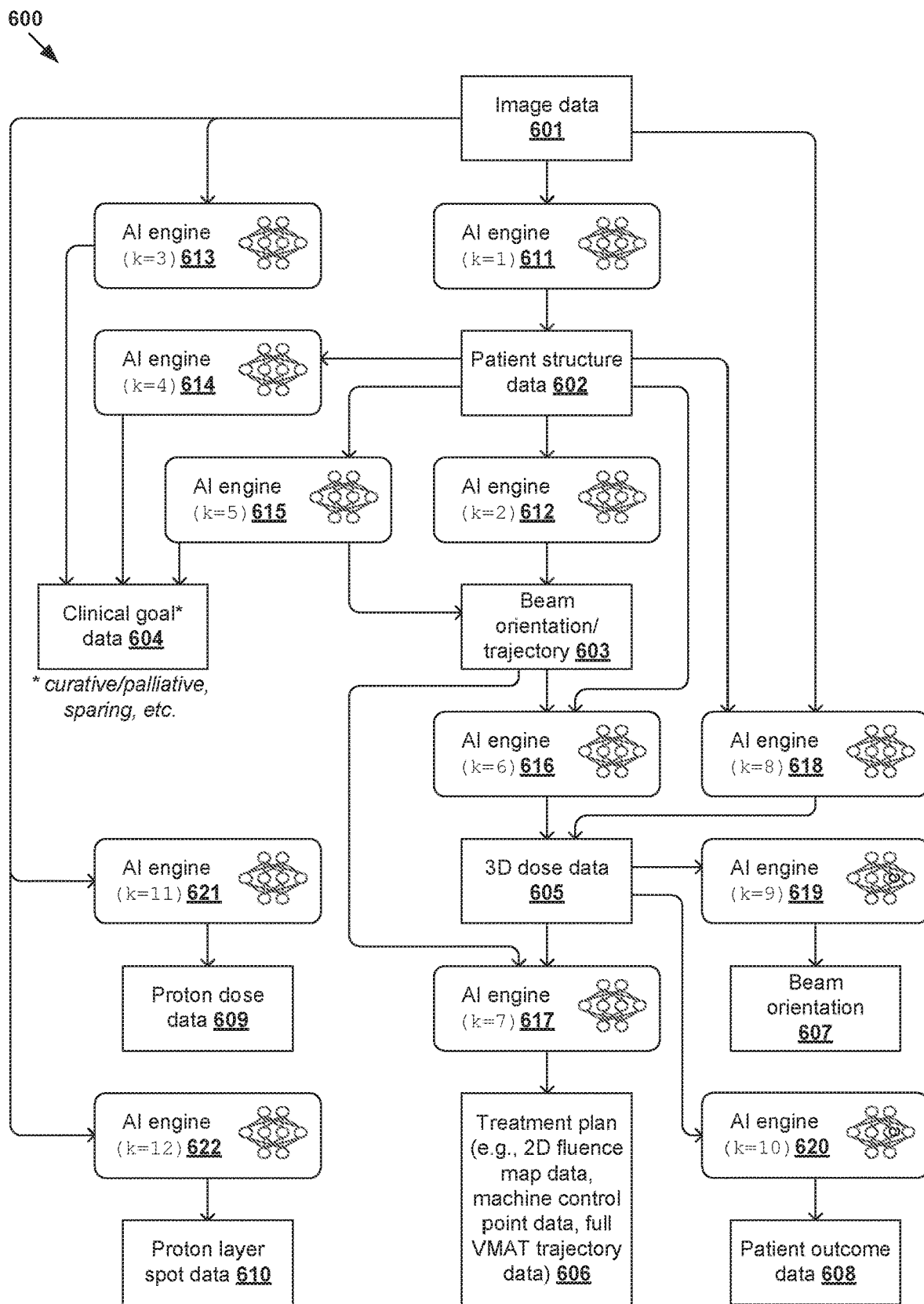
FIG. 6 is a schematic diagram illustrating a second example inferential chain that includes multiple AI engines for radiotherapy treatment planning.

Additional example AI engines and treatment planning steps are shown in FIG. 6, which is a schematic diagram illustrating a second example inferential chain that includes multiple AI engines for radiotherapy treatment planning. It should be understood that AI engines 611-622 (i.e., K=12) are shown to illustrate example steps or intermediate steps that may be performed during radiotherapy treatment planning, and it is not necessary to include all AI engines 611-622 in the same inferential chain. The various steps in FIG. 4 and FIG. 6 may be combined into fewer steps, divided into additional steps, and/or eliminated based upon the desired implementation.

AI engines 611-622 may be trained using any suitable training data and/or statistical model(s), and validated using statistical model(s) and/or validation data according to the example in FIG. 3. In practice, AI engines 611-622 may be trained separately using different training sets of input and output data to identify an optimal breakdown of steps required for a given clinical case category or individual training set. The training of various independent AI engines may be used as a form of validation of the resulting inferential chain.

At k=1 in FIG. 6, AI engine 611 may be trained to perform segmentation to generate output data=patient structure data 602 based on input data=image data 601. At k=2 in FIG. 6, AI engine 612 may be trained to generate output data=beam orientation/trajectory data 603 based on input data=patient structure data 602. AI engines 611-612 in FIG. 6 are similar to respective AI engines 430, 450 in FIG. 4, whose training and validation approaches are also applicable here. For example, the training data may include image data, segmentation results, fully-optimized treatment delivery plan, or any combination thereof. Validation may further involve statistical analysis (e.g., using RapidPlan™ available from Varian Medical Systems, Inc.), deliverability check(s), analysis of the time required to delivery plan, collision check(s), DVH check(s). The idea is that patient structure data 602 may be used to drive beam/trajectory locations to create 3D dose data 605 (e.g., dose distributions) that better conform to the target volume while avoiding OARs.

AI engines 613-615 may be used to generate clinical goal data 604, such as data relating to curative/palliative goal(s), dose sparing goal(s), etc. For example, a clinical goal may be a clinical decision to save or sacrifice an OAR (e.g., parotid gland), in which case the set of clinical goals may be discrete. In another example, a clinical goal may be expressed using continuous values, such as dose levels, etc. In a further example, a clinical goal may represent a trade-off or balance between competing objectives, such as dose sparing of OAR and better target coverage, dose sparing of multiple OARs, etc. The trade-off may be one-to-one, one-to-many, or many-to-many.

In more detail, at k=3 in FIG. 6, AI engine 613 may be trained to generate output data=clinical goal data 604 based on input data=image data 601 (e.g., 3D CT images). The input data may also include data relating to the treatment (e.g., radiation, surgery, chemotherapy, immune, etc.) prescribed to the patient. In this case, the training data may also include patient-related data, including but not limited to genetic data, disease stage, patient clinical history, biopsy results, cancer genetic analysis or genetic assays, patient genetic assays, etc.). Validation data may include similar patient-related data, but extracted from different patients. Additional useful data would include long-term clinical data (e.g. 5-year survival rate). Any suitable statistical model(s) may be used during training and/or validation, such as a conditional probability of a certain clinical decision if a pre-determined condition is occurring.

At k=4 in FIG. 6, AI engine 614 may be trained to generate clinical goal data 604 based on input data=patient structure data 602. Compared to AI engine 613 (k=3), clinical goal data 604 generated using AI engine 614 (k=4) should be more refined because geometric data about the patient anatomy may be used to predict dose levels that can be achieved within OARs given their location relative to the target volume. This results in more refined clinical goals that are personalized for a particular patient. Any suitable statistical model(s) during validation, such as the probability of a decision to spare parotid gland when the distance between parotid gland volumetric center and a target edge is known. Further, at k=5, AI engine 615 may be trained to generate clinical goal data 604 and beam orientation/trajectory data 603 based on input data =patient structure data 602. Any combination of the training data, statistical model(s) and other validation data discussed above may be used.

In practice, there is an emerging field of radiomics that attempts to identify image features that are predictive of patient outcome. Foreknowledge of the potential outcome, and the key drivers of the outcome may, in some instances, inform the treatment decision and modulate the standard treatment prescription. Thus, AI engines 613-615 may be used as decision support tools to assist physicians to determine the best course of treatment for a given patient, including such fundamental questions as whether this patient should be treated with curative intent vs palliative intent. AI engines 613-615 may be trained to assess, for example, whether a patient may be treated with radiotherapy (and optionally with other modalities such as surgery, chemotherapy, immune, etc.). In general, a patient treated with a palliative intent may not need dose to be as conformal as a patient with a curative intent, and this will change the clinical goals in terms of prescription, fractionation, etc. Additional patient-related data may be used to train an AI engine to determine and recommend prescription, fractionation, OAR dose limits, alternative treatment (e.g., chemotherapy, surgery, immune, etc.).

At k=6 in FIG. 6, AI engine 616 may be trained to generate output data=3D dose data 605 based on input data=patient structure data 602 and beam orientation/trajectory data 603. Compared to the example in FIG. 4, AI engine 616 may be trained to perform 3D dose prediction after beam geometry has been defined using AI engine 612. In particular, a protocol selection step (e.g., includes the selection of fractionation scheme and other clinical goals) may be performed after beam orientation/trajectory data 603 is, at least, partially defined.

At k=7 in FIG. 6, AI engine 617 may be trained to generate output data=treatment plan 606 based on input data=beam orientation/trajectory data 603 and 3D dose data 605. Treatment plan 606 may include 2D fluence map, full VMAT trajectory data, or machine control data. Similar to AI engine 470 in FIG. 4, the training data may include patient data with segmentation(s) and treatment plan(s). Validation may be performed using DVH, knowledge-based planning systems (e.g., RapidPlan™ available from Varian Medical Systems, Inc.), dose gradient, OAR dose limits, target dose prescription, total leaf motion, any combination thereof, etc. A forward dose calculation algorithm may be used to verify that the 2D fluence maps and beam orientations produce the predicted 3D dose.

At k=8 in FIG. 6, AI engine 618 may be trained to generate output data=3D dose data 605 based on input data=image data 601 and patient structure data 602. In some instances, AI engine 618 may be used to infer the principal shape of the 3D dose distribution without knowledge of the specific beam orientations, as many IMRT solutions are degenerate when looking at the 3D dose in the neighborhood of the tumor.

At k=9 in FIG. 6, AI engine 619 may be trained to generate output data=beam orientation data 607 based on input data=3D dose data 605. In this case, AI engine 619 may be used to select beam orientations that produce dose distributions that adequately match the principle shape of the predicted 3D dose. At k=10 in FIG. 6, AI engine 620 may be trained to predict output data=patient outcome data based on input data=3D dose data 605. Validation may be performed using historical normal tissue complication probability, tumor control probabilities, etc.

Additionally or alternatively, AI engines 621-622 may be trained to implement proton therapy treatment planning. For example, at k=11 in FIG. 6, AI engine 621 may be trained to generate output data=proton dose data 609 based on input data=image data 601 for use during proton dose planning. At k=12, AI engine 622 may be trained to generate output data=proton layer spot data 610 based on input data=image data 601 for use during energy layer spot planning. This reflects a different planning and delivery paradigm of a scanning proton beam relative to a proton delivery system with MLC. For proton delivery, the final treatment plan may include beam orientation/trajectory data, energy election data, spot size data, scanning pattern data, energy switch data, etc. The target volume may be broken into layers, and each layer may be learned in a similar manner as to how a single fluence map for photons is learned. A proton plan may need to learn several layers per beam orientation. AI engine 621/622 may be used in a parallel process to creating beam orientation/trajectory, fluence maps, etc.

Note that any of AI engines 611-622 may include multiple sub-engines. For example, AI engine 621/622 may include sub-engines for performing segmentation, field geometry definition, optimization object definition, machine parameter definition, any combination thereof. While a photon beam is generally assumed to utilize a single energy mode, the photon beam may include several different energy layers. Spot weights in different energy layers may be considered to be similar to photon fluence. Further, in practice, examples of the present disclosure may be implemented to generate treatment plan(s) for other treatment delivery system(s), such as particle therapy treatment plans for particle delivery systems (e.g., carbon ion, etc.).

During the inference phase, it is possible that an AI engine encounters a patient or situation that falls outside of its training experience, and predicts a result that is not consistent with historical data. In this case, the AI engine may be flagged either as not having a high confidence level, by disagreeing with the statistical validation model, and/or identified by human operator as not meeting specifications. Also, new dataset may be added to the training set, and the AI engine re-trained such that it learns from this new situation.

AI Engine Aggregation

According to examples the present disclosure, an AI engine may be trained to emulate a particular treatment planner performing a treatment planning step. The goal is to predict, replicate or mimic the clinical practices, actions or behavior of the planner. As used herein, the term "treatment planner" (or more simply "planner") may refer to an individual (e.g., clinical expert), a group of individuals, a clinical site or institution (e.g., research institution, university), a network of sites, etc. For a particular group, site, institution or network of sites, there may be standards and/or practices that are enforced within the site or network. Depending on the desired implementation, a "treatment planner" may also be a computer system with hardware and/or software capable of performing treatment planning step(s).

Figure 7:
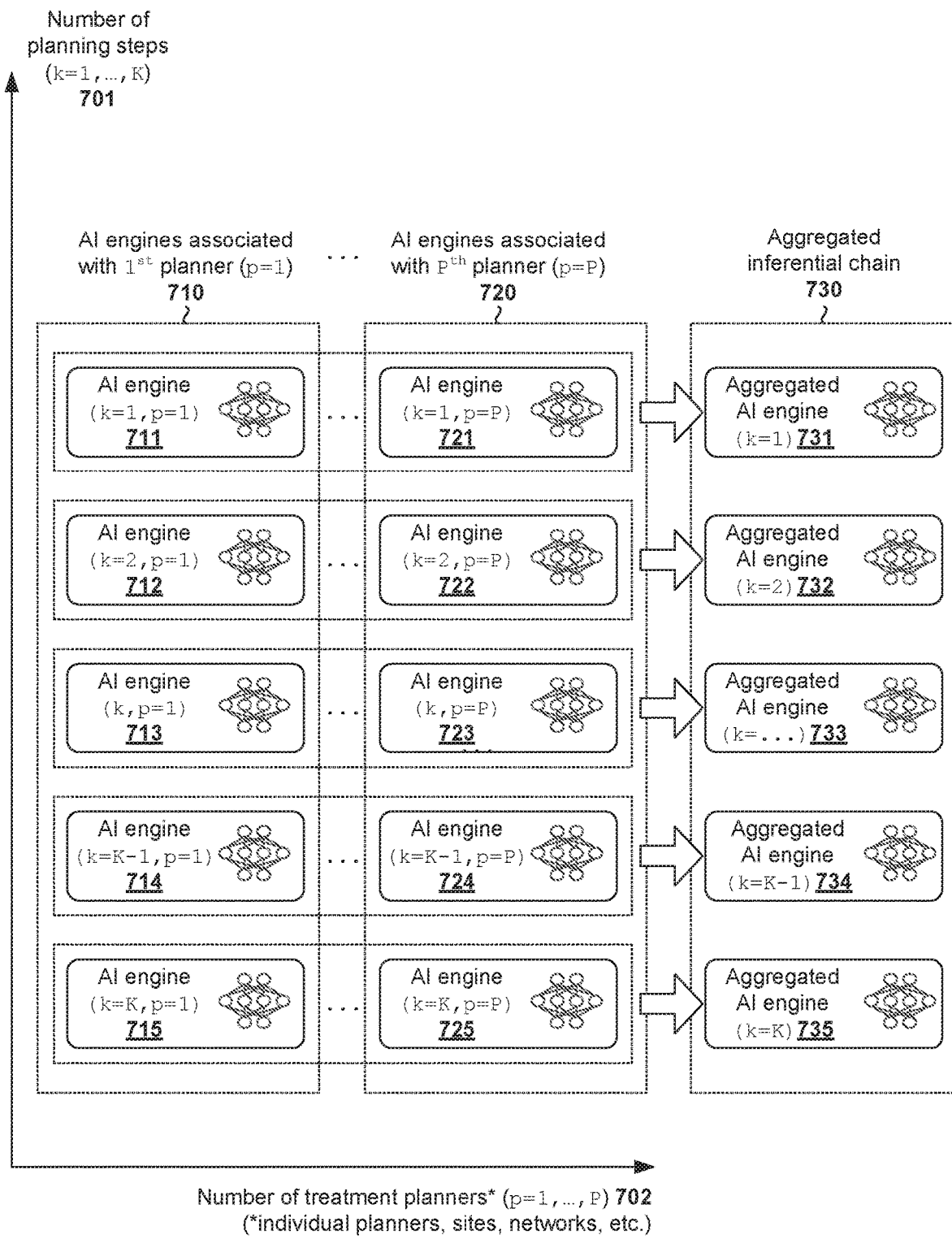
FIG. 7 is a schematic diagram illustrating example AI engines associated with different treatment planners.

Some examples are shown in FIG. 7, which is a schematic diagram illustrating example AI engines associated with different treatment planners. Here, the number of planners is denoted as P and a particular planner may be the $p^{th}$ planner ($p \in \{1,2,\ldots,P\}$). For example, AI engines (see 711-715) are associated with a first planner (p=1), while AI engines (see 721-725) are associated with the $P^{th}$ planner. AI engines 711-715 may form an inferential chain (see 710), and AI engines 721-725 forming another inferential chain (see 720). Although not shown for simplicity, an inferential chain may include AI engines associated with a combination of planners.

In the example in FIG. 7, if a radiotherapy treatment planning process is divided into K steps (see 701) and there are P planners (see 702) with different clinical practices, a total of P×K AI engines may be trained. As discussed using FIG. 1, this reflects the lack of "gold standard" for radiotherapy treatment planning. For example, for a particular treatment planning step such as segmentation (k=1), there is generally a lack of consensus among different planners (p=1,2,\ldots,P) as to what constitutes "good" contours or segments. As such, although trained to perform the same step, AI engine 711 associated with the first planner (p=1) might produce vastly different results compared to AI engine 721 associated with the $P^{th}$ planner.

According to a second aspect of the present disclosure, multiple AI engines associated with different treatment planners may be aggregated to form an aggregated AI engine. For example in FIG. 7, first aggregated AI engine 731 may be formed by aggregating multiple AI engines 711-721 that each are trained to perform a first treatment planning step (k=1). Each of AI engines 711-712 emulates a particular planner performing the first treatment planning step, including AI engine 711 emulating the first planner (p=1) and AI engine 721 emulating the $P^{th}$ planner. Similarly, second aggregated AI engine 732 may be formed by aggregating multiple AI engines (e.g., 712, 722) that are trained to perform a second treatment planning step (k=2). See also aggregated AI engines 733-735 for other values of k. An inferential chain may include one aggregated AI engine, or multiple aggregated AI engines 731-735 (forming aggregated inferential chain 730).

Figure 8:
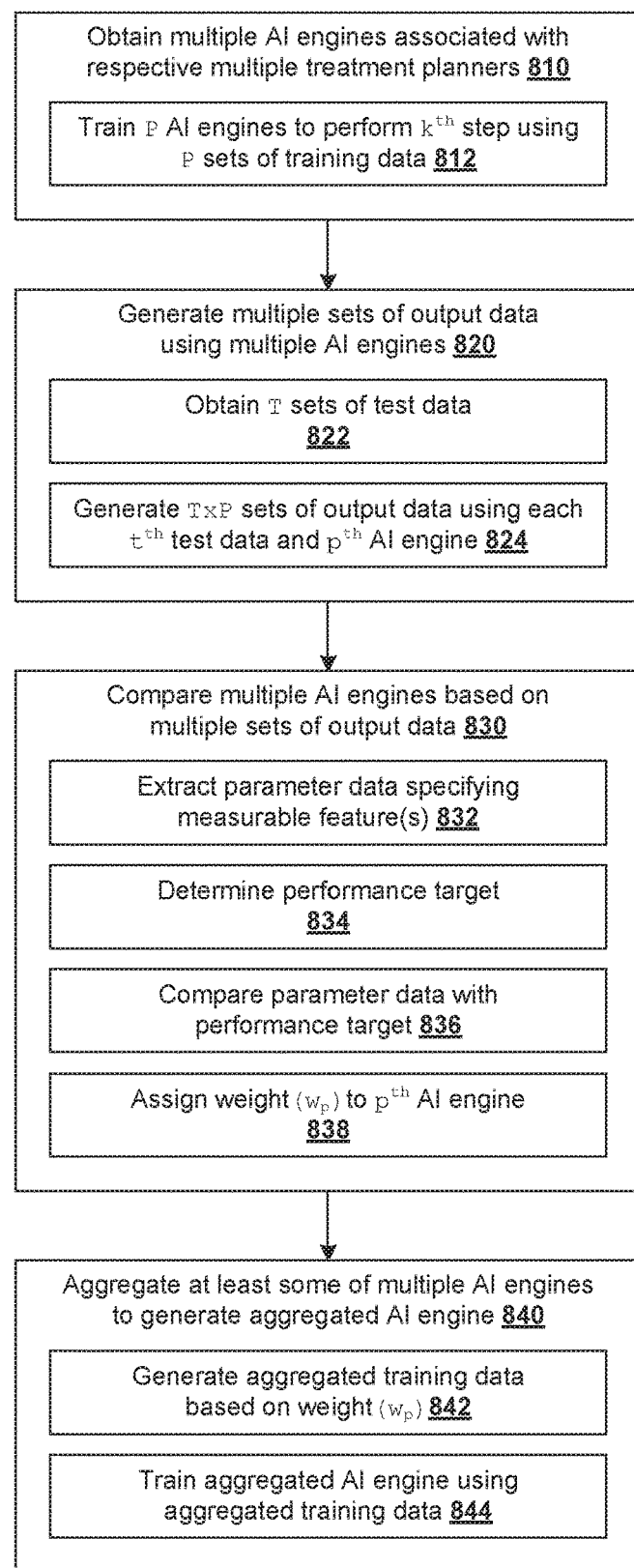
FIG. 8 is a flowchart of an example process for a computer system to generate an aggregated AI engine for radiotherapy treatment planning.

In more detail, FIG. 8 is a flowchart of example process 800 for a computer system to generate an aggregated AI engine for radiotherapy treatment planning. Example process 800 may include one or more operations, functions, or actions illustrated by one or more blocks, such as 810 to 844. The various blocks may be combined into fewer blocks, divided into additional blocks, and/or eliminated based upon the desired implementation. Example process 800 may be implemented using any suitable computer system, an example of which will be discussed using FIG. 12.

At 810 in FIG. 8, multiple AI engines (e.g., 711-721 in FIG. 7) associated with respective multiple treatment planners (e.g., p=1,\ldots,P) are obtained. Here, the term "obtain" is used broadly to include, for example, training the AI engine using training data according to the example in FIG. 3. Another example of "obtain" is the computer system accessing or retrieving computer-readable instructions associated with trained AI engines (e.g., from local or remote storage), etc. At 820, multiple sets of output data may be generated using the multiple AI engines. At 830 and 840, the multiple AI engines may be compared based on the multiple sets of output data and, based on the comparison, at least some of the multiple AI engines may be aggregated to form an aggregated AI engine (e.g., 731) for performing the particular treatment planning step.

Figure 9:
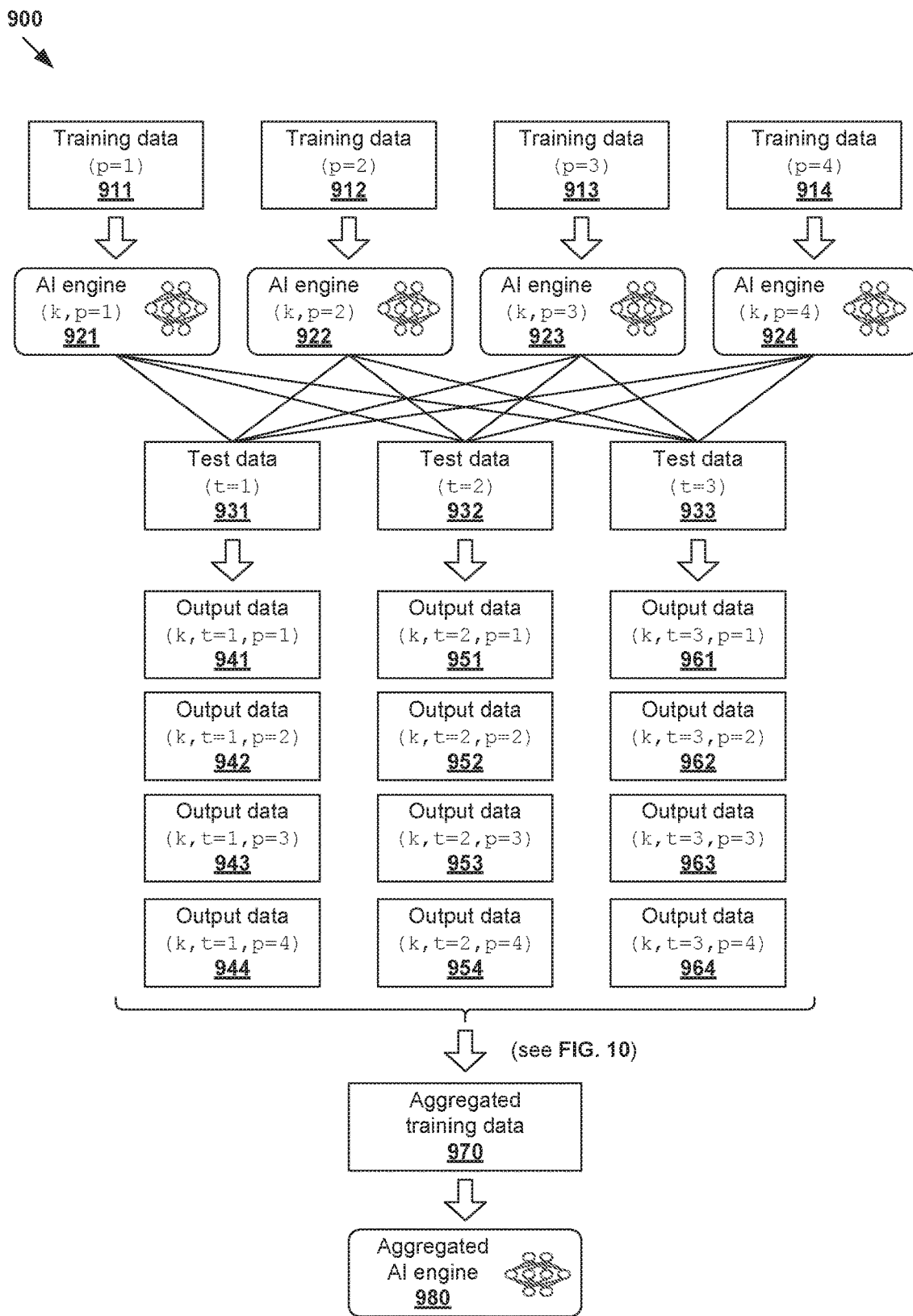
FIG. 9 is a schematic diagram illustrating a detailed example of AI engine aggregation according to the example in FIG. 8.

Some detailed examples of blocks 810-840 in FIG. 8 will be discussed using FIG. 9 and FIG. 10. FIG. 9 is a schematic diagram illustrating example AI engine aggregation 900 according to the example in FIG. 8, and FIG. 10 is a schematic diagram illustrating example AI engine comparison 1000 according to the example in FIG. 8. Note that AI engines 921-924 in FIG. 9 may be trained to perform a particular treatment planning step, such as segmentation (k=1) to generate patient structure data based on image data;

3D dose prediction (k=2) to generate 3D dose data based on patient structure data; structure projection estimation (k=3) to generate structure projection data (e.g., beam orientation/trajectory) to deliver 3D dose data; or treatment plan generation (k=4) to generate treatment plan 150 in FIG. 4. Any of the examples in FIG. 6 may also be implemented, such as clinical goal estimation, patient outcome prediction, proton dose estimation, proton layer spot data estimation, etc.

(a) AI Engines (Block 810)

Referring first to FIG. 9, consider a scenario where four AI engines (see 921-924 in FIG. 9) are trained to emulate four treatment planners (P=4), respectively. To train AI engines 921-924, multiple sets of training data associated with respective P planners may be used. For example, first set of training data 911 is associated with a first planner (p=1), second set of training data 922 is associated with a second planner (p=2), third set of training data 923 with a third planner (p=3), and fourth set of training data 924 with a fourth planner (p=4). Each set of training data may include any suitable number of training cases.

To emulate a particular planner (denoted as p), one approach is to train an AI engine using training data generated by the planner, such as based on patient structure data, 3D dose data, structure projection data, treatment plans of past patients, etc. In the case of segmentation (k=1), each set of training data may include patient structure data specifying target(s) and OAR(s) identified by a particular planner for past patients. Statistical model(s) and/or validation data used during the training phase may also be designed based on the planner. Another approach to emulate a particular planner is by adjusting a (pre-trained) general AI engine to reflect decisions made by the planner, such as by augmenting the training data, reinforcing the learning process by observing the decisions of the planner, etc. See also corresponding 812 in FIG. 8.

(b) Output Data (Block 820)

AI engines 921-924 may be used to generate multiple sets of output data 941-964. One approach involves using multiple sets of test data to test AI engines 921-924, such as three sets (T=3) 931-933 in FIG. 9. In this case, each $p^{th}$ AI engine is used to generate output data using each $t^{th}$ set of test data (i.e., as input data), where $p \in \{1,2, \ldots, P\}$ and $t \in \{1,2, \ldots, T\}$. This generates a total of T×P=12 sets of output data representing variants associated with different planners. For example, output data 941-944 is generated using first set of test data 931 (t=1), output data 951-954 using second set of test data 932 (t=2), and output data 961-964 using third set of test data 933 (t=3). See also corresponding 822 and 824 in FIG. 8.

(c) Comparison (Block 830)

Next, AI engines 921-924 may be compared based on the T×P=12 sets of output data 941-964. In practice, the comparison at block 830 may be performed using any suitable techniques, such as machine learning, statistics, non-dimensional analysis, statistical model(s), clustering, geometric comparison, etc. Any suitable geometric comparison approach may be used, such as gamma analysis, Sorensen-Dice similarity coefficient for image segmentation, etc. Some examples will be explained below using FIG. 8 and FIG. 10.

At 832 in FIG. 8, parameter data (see 1011-1034 in FIG. 10) specifying one or more measurable features or quantities associated with output data 941-964 may be identified or extracted. For example, in the case of segmentation (k=1), a statistical model may be used to evaluate the shape of a target (e.g., prostate) identified in output data 941-964 by respective AI engines 921-924. In this case, parameter data 1011-1034 may include a sphericity or roundness measure of the target. Another statistical model may be used to measure the distance between the target (e.g., prostate) and OAR (e.g., rectum). This way, parameter data 1011-1034 represents common parameter(s) for assessing whether AI engines 921-924 emulating different planners segment a given patient in the same manner and produce the same contours.

In the case of 3D dose prediction (k=2), a statistical model may be used to measure a dose level (e.g., minimum, maximum, mean) of a target or OAR in output data 941-964 generated by respective AI engines 921-924. In this case, parameter data 1011-1034 may include parotid gland mean dose level, spinal cord maximum dose level, etc. Another statistical model may measure the target dose coverage. Parameter data extracted from the output data generated by the $p^{th}$ AI engine based on the $t^{th}$ set of test data may be a scalar or vector denoted as $x_{tp}$, where $p \in \{1,2, \ldots, P\}$ and $t \in \{1,2, \ldots, T\}$. In practice, multiple statistical models may be combined into multi-parametric model for identifying parameter data 1011-1034. Statistical models may also be used to determine which, if any, of the planners are outliers and reduce the weight of their contribution in the final aggregated AI engine.

At 834, 836 and 838 in FIG. 8, a performance target representing the "consensus truth" among different planners may be determined, and compared with parameter data 1011-1034 to assign a score or weight ($w_p$) to each $p^{th}$ AI engine ($p \in \{1,2, \ldots, P\}$). Appreciating that there are several schools of thought about the ideal radiotherapy treatment planning strategy, and that actual patient outcome data may not be available for many years, the consensus truth may be used as a surrogate for ground truth. Here, the ground truth may represent an objective correct output. For example, training data 911-914 used during training may represent the ground truth because AI engines 921-924 are trained to emulate different planners. In unsupervised learning, there is generally no ground truth, but instead the consensus truth may be established based on the majority (or average) action of the planners. Comparing the prediction (i.e., output data and parameter data) of AI engines 921-924 is generally more accurate than comparing original training data 911-914 because the treated patients may be different.

The performance target may be determined based on output data 941-964, such as parameter data 1011-1034 extracted from output data 941-964, etc. For example, in the case of segmentation (k=1), the performance target may be a sphericity measure of target=prostate (e.g., 80% spherical). In the case of 3D dose prediction (k=2), the performance target may be a combination of the following: parotid gland mean dose level less than 20 Gy, spinal cord maximum dose level less than 40 Gy, target dose coverage more than 85%, etc. A simple approach for establishing the consensus truth would be to determine an average value or weighted average value based on parameter data 1011-1034. In the latter case, the weights may be based on any suitable factor(s), such as reputation of the corresponding $p^{th}$ planner in the community, the expert option of an individual reviewing the results, etc.

Another approach is to generate a distribution generated based on parameter data 1011-1034. The distribution may be unidimensional or multidimensional. In one example in FIG. 10, the distribution may be unimodal (see 1040), such as a normal distribution around a mean or median value (y1). The unimodal distribution indicates that a similar clinical objective has been used by the different planners emulated by respective AI engines 921-924. For example, in prostate cancer treatment, different planners might agree that the clinical objective would be to minimize the volume in rectum and bladder getting a high dose level (in addition to the target dose coverage). However, the exact trade-off or balance between the two OARs might vary, resulting in deviation of parameter data 1011-1034 from performance target=mean or median value (y1). In this case, a score or weight ($w_p$) may be assigned to the $p^{th}$ AI engine based on the deviation or distance from y1. See also 1050 in FIG. 10.

In another example in FIG. 10, the distribution may be multimodal (see 1060), which is a distribution with multiple modes or peaks. The multimodal distribution indicates that different clinical objectives have been used by the planners. For example, in more complicated head and neck treatment, some planners try to reduce the dose to pharyngeal constrictor muscles, while some other planners do not. The different clinical practices might be manifested as multimodal distribution 1060 in mean dose having two peaks at z1 and z2, respectively. In this case, clustering may be performed to assign AI engines 921-924 to different clusters. See also 1070 in FIG. 10.

For example, based on multimodal distribution 1060, two clusters may be formed. In this case, a score or weight ($w_p$) may be assigned to the $p^{th}$ AI engine by identifying a cluster to which it is assigned, and comparing its parameter data to a mean value (e.g., z1 or z2) associated with the cluster. Depending on the desired implementation, cluster membership may be expressed as a probability, which may be used to influence the weight assignment. Also, some form of adjudication may be performed to assess whether there actually is a ground truth among or between the clusters, or whether there are genuinely different ground truths. The adjudication may be manual or automated.

(d) Aggregation (Block 840)

Based on the above comparison, at least some of AI engines 921-924 (e.g., all AI engines or some assigned to a cluster) may be aggregated to form aggregated AI engine 980. The aggregation process may include generating aggregated training data 970 based on training data 911-914, and training aggregated AI engine 980 using aggregated training data 970. See corresponding 842 and 844 in FIG. 8. For the first example in FIG. 10 (see 1040-1050), aggregated training data 970 may be a weighted combination of training data 911-914 according to the weights ($w_p$) assigned to respective AI engines 921-924.

For the second example (see 1050-1070), aggregated training data 970 may be generated by combining training data associated with AI engines assigned to a particular cluster. If AI engines 921-922 (p=1 and p=2) are assigned to a first cluster, aggregated training data 970 may be generated based a weighted combination of corresponding training data 911-912 according to their respective weights ($w_p$). Multiple aggregated AI engines may also be generated. For example, if AI engines 923-924 (p=3 and p=4) are assigned to a second cluster, another aggregated AI engine may be trained using a weighted combination of training data 913-914.

Depending on the desired implementation, aggregated AI engine 980 may be trained according to the example in FIG. 3. Although not shown for simplicity, any suitable statistical model(s) and validation data may be used during the training phase. In practice, temporal information may be added to AI engines 921-924 to take into account of evolving clinical goals and consensus truth as the standards of treatment planning shift and improve over time. In this case, AI engines trained using older training data may be assigned with a lower weight compared to those trained using newer training data. The adjustment maybe considered during the training of aggregated AI engine, or during the definition of the consensus truth in FIG. 10. For example, a four-field box plan was once the standard of care, but is now considered to be a bad plan relative to IMRT or VMAT. As plan quality improves and new delivery techniques become the new standard, the newer, higher quality plans may be given more weight in training AI engines than older, lower quality plans.

Once trained and validated, aggregated AI engine 980 may be used to perform a particular treatment planning step during the inference phase. For example, FIG. 11 is a flowchart of example process 1100 for a computer system to perform radiotherapy treatment planning using an aggregated AI engine. Example process 1100 may include one or more operations, functions, or actions illustrated by one or more blocks, such as 1110 to 1140. The various blocks may be combined into fewer blocks, divided into additional blocks, and/or eliminated based upon the desired implementation. Examples of the present disclosure may be implemented using any suitable computer system, an example of which will be discussed using FIG. 12.

At 1110 in FIG. 11, image data 120 associated with a patient requiring treatment may be obtained. At 1120 in FIG. 11, image data 120 may be processed using inferential chain 140 to generate treatment plan 150 for the patient. Inferential chain 140 includes multiple AI engines 141-14K, where each $k^{th}$ AI engine may be trained separately to perform a $k^{th}$ treatment planning step of the planning process (k=1, 2, . . . , K). At least one of AI engines 141-14K may be aggregated AI engine 980 that is generated according to the examples in FIG. 8-10.

For example, at 1130 in FIG. 11, aggregated AI engine 980 may perform a first treatment planning step to generate first output data based on (i) image data 120 or (ii) first input data generated based on image data 120. Alternatively, at 1140 in FIG. 11, aggregated AI engine 980 may perform a second treatment planning step to generate treatment plan 150 based on (i) the first output data of the first AI engine or (ii) second input data generated based on the first output data. Inference chain 140 may also include at least one other AI engine, which may be an aggregated AI engine or trained to emulate a particular planner.

Computer System

The above examples can be implemented by hardware, software or firmware or a combination thereof. FIG. 12 is a schematic diagram of example computer system 1200 for radiotherapy treatment planning. In this example, computer system 1205 (also known as a treatment planning system) may include processor 1210, computer-readable storage medium 1220, interface 1240 to interface with radiotherapy treatment system 160, and bus 1230 that facilitates communication among these illustrated components and other components.

Processor 1210 is to perform processes described herein with reference to FIG. 1 to FIG. 11. Computer-readable storage medium 1220 may store any suitable information 1222, such as information relating to training data, statistical model(s), validation data, test data, AI engines, etc. Computer-readable storage medium 1220 may further store computer-readable instructions 1224 which, in response to execution by processor 1210, cause processor 1210 to perform processes described herein. Treatment may be delivered according to treatment plan 150 using treatment system 160 explained using FIG. 1, the description of which will not be repeated here for brevity.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. Throughout the present disclosure, the terms "first," "second," "third," etc. do not denote any order of importance, but are rather used to distinguish one element from another.

Those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure.

Although the present disclosure has been described with reference to specific exemplary embodiments, it will be recognized that the disclosure is not limited to the embodiments described, but can be practiced with modification and alteration within the spirit and scope of the appended claims. Accordingly, the specification and drawings are to be regarded in an illustrative sense rather than a restrictive sense.

We claim:

1. A method for a computer system to perform radiotherapy treatment planning, wherein the method comprises:
   obtaining image data associated with a patient; and
   processing the image data to generate a treatment plan for the patient using an inferential chain that includes multiple artificial intelligence (AI) engines that are trained separately to perform respective multiple treatment planning steps, wherein the image data is processed by:
      performing, using a first AI engine from the multiple AI engines, a first treatment planning step to generate first output data based on at least one of: (i) the image data, and (ii) first input data generated based on the image data; and
      performing, using a second AI engine from the multiple AI engines, a second treatment planning step to generate the treatment plan based on at least one of: (i) the first output data, and (ii) second input data generated based on the first output data.

2. The method of claim 1, wherein the method further comprises at least one of the following:
   prior to processing the image data, validating the first AI engine using one or more first statistical models or first validation data, to determine whether the first AI engine satisfies one or more first validation criteria; and
   prior to processing the image data, validating the second AI engine using one or more second statistical models or second validation data, to determine whether the second AI engine satisfies one or more second validation criteria.

3. The method of claim 2, wherein the method further comprises at least one of the following:
   validating the first AI engine using the one or more first statistical models that evaluate at least one of the following: dose level of a structure identified from the image data, size of the structure, shape of the structure, texture of the structure, principal component analysis of the structure, geometric distribution of the structure, material density in the structure, and distance between multiple structures identified from the image data; and
   validating the second AI engine using the one or more second statistical models that evaluate at least one of the following: smoothness of two-dimensional (2D) fluence map data, and total motion of leaves in volumetric modulated arc therapy (VMAT) trajectory data.

4. The method of claim 1, wherein the method further comprises at least one of the following:
   prior to processing the image data, training the first AI engine to perform the first treatment planning step using first training data, or one or more first statistical models, or both; and
   prior to processing the image data, training the second AI engine to perform the second treatment planning step using second training data, or one or more second statistical models, or both.

5. The method of claim 1, wherein performing the second treatment planning step comprises:
   performing treatment plan generation to generate the treatment plan for treatment delivery using a treatment system, wherein the treatment plan includes one of the following: 2D fluence map data, VMAT trajectory data and machine control point data.

6. The method of claim 5, wherein performing the first treatment planning step comprises one of the following:
   based on the image data, performing segmentation to generate the first output data in the form of structure data;
   based on the structure data, performing three-dimensional (3D) dose shaping to generate the first output data in the form of 3D dose data associated with the structure data;
   based on the structure data and the 3D dose data, performing structure projection estimation to generate the first output data in the form of structure projection data to deliver the 3D dose data;
   based on the image data or structure data, performing clinical goal estimation to generate the first output data in the form of clinical goal data;
   based on 3D dose data generated based on the image data, performing patient outcome prediction to generate the first output data in the form of patient outcome data;
   based on the image data, performing proton dose estimation to generate the first output data in the form of proton dose data; and
   based on the image data, performing proton layer spot data estimation to generate the first output data in the form of proton layer spot data.

7. The method of claim 1, wherein processing the image data comprises at least one of the following:
   performing the first treatment planning step using the first AI engine in the form of a first aggregated AI engine that is generated by aggregating multiple third AI engines that emulate respective multiple planners; and
   performing the second treatment planning step using the second AI engine in the form of a second aggregated AI engine that is generated by aggregating multiple fourth AI engines that emulate respective multiple planners.

8. A non-transitory computer-readable storage medium that includes a set of instructions which, in response to execution by a processor of a computer system, cause the processor to perform a method of radiotherapy treatment planning, the method comprising:

obtaining image data associated with a patient; and processing the image data to generate a treatment plan for the patient using an inferential chain that includes multiple artificial intelligence (AI) engines that are trained separately to perform respective multiple treatment planning steps, wherein the image data is processed by:

performing, using a first AI engine from the multiple AI engines, a first treatment planning step to generate first output data based on at least one of: (i) the image data, and (ii) first input data generated based on the image data; and performing, using a second AI engine from the multiple AI engines, a second treatment planning step to generate the treatment plan based on at least one of: (i) the first output data, and (ii) second input data generated based on the first output data.

9. The non-transitory computer-readable storage medium of claim 8, wherein the method further comprises at least one of the following:

prior to processing the image data, validating the first AI engine using one or more first statistical models or first validation data, or both, to determine whether the first AI engine satisfies one or more first validation criteria; and prior to processing the image data, validating the second AI engine using one or more second statistical models or second validation data, or both, to determine whether the second AI engine satisfies one or more second validation criteria.

10. The non-transitory computer-readable storage medium of claim 9, wherein the method further comprises at least one of the following:

validating the first AI engine using the one or more first statistical models that evaluate at least one of the following: dose level of a structure identified from the image data, size of the structure, shape of the structure, texture of the structure, principal component analysis of the structure, geometric distribution of the structure, material density in the structure, and distance between multiple structures identified from the image data; and validating the second AI engine using the one or more second statistical models that evaluate at least one of the following: smoothness of two-dimensional (2D) fluence map data, and total motion of leaves in volumetric modulated arc therapy (VMAT) trajectory data.

11. The non-transitory computer-readable storage medium of claim 8, wherein the method further comprises at least one of the following:

prior to processing the image data, training the first AI engine to perform the first treatment planning step using first training data, or one or more first statistical models, or both; and prior to processing the image data, training the second AI engine to perform the second treatment planning step using second training data, or one or more second statistical models, or both.

12. The non-transitory computer-readable storage medium of claim 8, wherein performing the second treatment planning step comprises:

performing treatment plan generation to generate the treatment plan for treatment delivery using a treatment system, wherein the treatment plan includes one of the following: 2D fluence map data, VMAT trajectory data and machine control point data.

13. The non-transitory computer-readable storage medium of claim 12, wherein performing the first treatment planning step comprises one of the following:

based on the image data, performing segmentation to generate the first output data in the form of structure data;

based on the structure data generated based on the image data, performing three-dimensional (3D) dose shaping to generate the first output data in the form of 3D dose data associated with the structure data;

based on the structure data and the 3D dose data, performing structure projection estimation to generate the first output data in the form of structure projection data to deliver the 3D dose data;

based on the image data or structure data, performing clinical goal estimation to generate the first output data in the form of clinical goal data;

based on 3D dose data generated based on the image data, performing patient outcome prediction to generate the first output data in the form of patient outcome data;

based on the image data, performing proton dose estimation to generate the first output data in the form of proton dose data; and based on the image data, performing proton layer spot data estimation to generate the first output data in the form of proton layer spot data.

14. The non-transitory computer-readable storage medium of claim 8, wherein processing the image data comprises at least one of the following:

performing the first treatment planning step using the first AI engine in the form of a first aggregated AI engine that is generated by aggregating multiple third AI engines that emulate respective multiple planners; and performing the second treatment planning step using the second AI engine in the form of a second aggregated AI engine that is generated by aggregating multiple fourth AI engines that emulate respective multiple planners.

15. A computer system configured to perform radiotherapy treatment planning, the computer system comprising:

a processor; and a non-transitory computer-readable medium having stored thereon instructions that, when executed by the processor, cause the processor to:

obtain image data associated with a patient; and process the image data to generate a treatment plan for the patient using an inferential chain that includes multiple artificial intelligence (AI) engines that are trained separately to perform respective multiple treatment planning steps, wherein the image data is processed by:

perform, using a first AI engine from the multiple AI engines, a first treatment planning step to generate first output data based on at least one of: (i) the image data, and (ii) first input data generated based on the image data; and perform, using a second AI engine from the multiple AI engines, a second treatment planning step to generate the treatment plan based on at least one of: (i) the first output data, and (ii) second input data generated based on the first output data.

16. The computer system of claim 15, wherein the instructions further cause the processor to perform at least one of the following:

prior to processing the image data, validate the first AI engine using one or more first statistical models or first validation data, or both, to determine whether the first AI engine satisfies one or more first validation criteria; and prior to processing the image data, validate the second AI engine using one or more second statistical models or second validation data, or both, to determine whether the second AI engine satisfies one or more second validation criteria.

17. The computer system of claim 16, wherein the instructions further cause the processor to perform at least one of the following:

validate the first AI engine using the one or more first statistical models that evaluate at least one of the following: dose level of a structure identified from the image data, size of the structure, shape of the structure, texture of the structure, principal component analysis of the structure, geometric distribution of the structure, material density in the structure, and distance between multiple structures identified from the image data; and validate the second AI engine using the one or more second statistical models that evaluate at least one of the following: smoothness of two-dimensional (2D) fluence map data, and total motion of leaves in volumetric modulated arc therapy (VMAT) trajectory data.

18. The computer system of claim 15, wherein the instructions further cause the processor to perform at least one of the following:

prior to processing the image data, train the first AI engine to perform the first treatment planning step using first training data, or one or more first statistical models, or both; and prior to processing the image data, train the second AI engine to perform the second treatment planning step using second training data, or one or more second statistical models, or both.

19. The computer system of claim 15, wherein the instructions for performing the second treatment planning step cause the processor to perform at least one of the following comprises:

perform treatment plan generation to generate the treatment plan for treatment delivery using a treatment system, wherein the treatment plan includes one of the following: 2D fluence map data, VMAT trajectory data and machine control point data.

20. The computer system of claim 19, wherein the instructions for performing the first treatment planning step cause the processor to perform at least one of the following comprises:

based on the image data, perform segmentation to generate the first output data in the form of structure data;

based on the structure data generated based on the image data, perform three-dimensional (3D) dose shaping to generate the first output data in the form of 3D dose data associated with the structure data;

based on the structure data and the 3D dose data, perform structure projection estimation to generate the first output data in the form of structure projection data to deliver the 3D dose data;

based on the image data or structure data, perform clinical goal estimation to generate the first output data in the form of clinical goal data;

based on 3D dose data generated based on the image data, perform patient outcome prediction to generate the first output data in the form of patient outcome data;

based on the image data, perform proton dose estimation to generate the first output data in the form of proton dose data; and based on the image data, perform proton layer spot data estimation to generate the first output data in the form of proton layer spot data.

21. The computer system of claim 15, wherein the instructions for processing the image data cause the processor to perform at least one of the following:

perform the first treatment planning step using the first AI engine in the form of a first aggregated AI engine that is generated by aggregating multiple third AI engines that emulate respective multiple planners; and perform the second treatment planning step using the second AI engine in the form of a second aggregated AI engine that is generated by aggregating multiple fourth AI engines that emulate respective multiple planners.

* * * * *